United States Patent
Myers et al.

(10) Patent No.: US 7,183,054 B2
(45) Date of Patent: Feb. 27, 2007

(54) ASSAY FOR IDENTIFYING BIOLOGICAL TARGETS OF POLYNUCLEOTIDE-BINDING COMPOUNDS

(75) Inventors: Andrew G. Myers, Boston, MA (US); Jacob R. LaPorte, Cambridge, MA (US); Chengguo Xing, Minneapolis, MN (US)

(73) Assignee: President and Fellows of Harvard College, Cambridge, MA (US)

( * ) Notice: Subject to any disclaimer, the term of this patent is extended or adjusted under 35 U.S.C. 154(b) by 586 days.

(21) Appl. No.: 10/453,243

(22) Filed: Jun. 3, 2003

(65) Prior Publication Data

US 2004/0248100 A1 Dec. 9, 2004

(51) Int. Cl.
*C12Q 1/68* (2006.01)
*C12Q 1/70* (2006.01)
*G01N 33/53* (2006.01)
*C07H 21/00* (2006.01)
*A61K 31/70* (2006.01)
*A61K 38/00* (2006.01)
*A01N 61/00* (2006.01)

(52) U.S. Cl. .................. 435/6; 536/23.1; 536/24.3; 530/300; 514/1; 514/44; 435/5; 435/7.1; 435/7.2

(58) Field of Classification Search .............. 435/6, 435/5, 7.1, 7.2; 536/23.1, 24.3; 530/300; 514/1, 44
See application file for complete search history.

(56) References Cited

U.S. PATENT DOCUMENTS

| | | | |
|---|---|---|---|
| 4,248,863 A | 2/1981 | Arai | 424/121 |
| 4,372,947 A | 2/1983 | Arai et al. | 424/121 |
| 4,419,732 A | 12/1983 | Lambregts et al. | 364/428 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,837,149 A | 6/1989 | Arai et al. | 435/119 |
| 4,973,679 A | 11/1990 | Caruthers et al. | 536/27 |
| 5,023,184 A | 6/1991 | Reichenbach et al. | 435/252.1 |

(Continued)

FOREIGN PATENT DOCUMENTS

DE   2 839 668   3/1979

(Continued)

OTHER PUBLICATIONS

Arai, et al., "Increased Production of Saframycin A and Isolation of Saframycin S". *The Journal of Antibiotics*, XXXIII(9): 951-960, 1980.

(Continued)

*Primary Examiner*—Jezia Riley
(74) *Attorney, Agent, or Firm*—Choate, Hall & Stewart LLP; C. Hunter Baker

(57) ABSTRACT

The present invention provides methods and systems for the identification of a biological target of a chemical compound, such as saframycin A, known to bind a polynucleotide. The invention also provides methods of screening chemical compounds for those which act in a similar method and may be more potent than known compounds. The inventive methods are particularly useful in the high-throughput screening of chemical compounds that target GAPDH. The invention also provides kits useful in the practice of the inventive method. Compounds identified by inventive methods are also included in the invention.

35 Claims, 10 Drawing Sheets

U.S. PATENT DOCUMENTS

| | | | | |
|---|---|---|---|---|
| 5,153,319 | A | 10/1992 | Caruthers et al. | 536/27 |
| 5,278,302 | A | 1/1994 | Caruthers et al. | 536/24.5 |
| 5,476,925 | A | 12/1995 | Letsinger et al. | 536/23.1 |
| 5,539,082 | A | 7/1996 | Nielsen et al. | 530/300 |
| 5,580,969 | A | 12/1996 | Hoke et al. | 536/24.5 |
| 5,639,612 | A * | 6/1997 | Mitsuhashi et al. | 435/6 |
| 5,646,260 | A | 7/1997 | Letsinger et al. | 536/23.1 |
| 5,652,355 | A | 7/1997 | Metelev et al. | 536/24.5 |
| 5,773,571 | A | 6/1998 | Nielsen et al. | 530/300 |
| 5,786,461 | A | 7/1998 | Buchardt et al. | 536/18.7 |
| 5,939,273 | A | 8/1999 | Lussow et al. | 435/7.1 |
| 6,027,879 | A * | 2/2000 | Lucas et al. | 435/6 |
| 6,124,292 | A | 9/2000 | Corey | 514/250 |
| 6,258,539 | B1 | 7/2001 | Hunkapiller et al. | 435/6 |

FOREIGN PATENT DOCUMENTS

| | | |
|---|---|---|
| EP | 173 649 | 3/1986 |
| EP | 0 233 841 | 8/1987 |
| EP | 0 329 606 | 8/1989 |
| JP | 56-135486 | 10/1981 |
| JP | 57-50896 | 3/1982 |
| JP | 61-58593 | 3/1986 |
| JP | 63-2991 | 1/1988 |
| WO | WO 92/05186 * | 4/1992 |
| WO | WO 98/12198 | 3/1998 |
| WO | WO 00/69862 | 11/2000 |
| WO | WO 01/19824 | 3/2001 |
| WO | WO 01/53299 | 7/2001 |

OTHER PUBLICATIONS

Arai, et al., "Directed Biosynthesis of New Saframycin Derivatives with Resting Cells of Streptomyces Lavendulae", *Antimicrobial Agents and Chemotherapy*, 28(1): 5-11, 1985.

Arai, T., "Isoquinolinequinones from Actinomycetes and Sponges", The Alkaloids, XXI: 56-100, 1983.

Arai, et al., "The Structure of a Novel Antitumor Antibiotic, Saframycin A", *Experientia*, 36:1025-1027, 1980.

Arai, et al., "Some Chemotherapeutic Properties of Two New Antitumor Antibiotics, Saframycins A and C", *Gann*, 71: 790-796, 1980.

Arai, et al., In Advances in Cancer Chemotherapy; University Park Press, Baltimore, 235-251, 1978.

Arai, et al., "New Antiobiotics Saframycins A, B, C, D and E", *The Journal of Antibiotics*, 30: 1015-1018, 1977.

Bowman, et al., "Pharmaceuticals of Ecteinascidin—743 (ET-743) in Three Phase Studies" *Ann. Oncol.* 9(Suppl 2): 119, 1998.

Davidson, B., "Renieramycin G, A New Alkaloid from the Sponge Xestospongia Caycedoi", *Tetrahedron Letters*, 33(26): 3721-3724, 1992.

Evans, et al., "Stereoselective Synthesis of (±)-Cyanocycline", *J. Am. Chem. Soc.* 108: 2478-2479, 1986.

Flanagan, et al., "Synthetic Studies in Quinocarcin: Total Synthesis of (±)-Quinocarcinamide vai Dipole Cycloaddition of an Azomethine Ylide Generated by NBS Oxidation", *J. Org. Chem.* 60: 6791-6797, 1995.

Fukuyama, et al., "A Stereocontrolled Total Synthesis of (±)-Renieramycin A", *Tetrahedron Letters*, 31(42): 5989-5992, 1990.

Ishiguro, et al., "Binding of Saframycin A, A Heterocyclic Quinone Anti-Tumor Antibiotic to DNA as Revealed by the Use of the Antibiotic Labeled with [$^{14}$C ] Tyrosine or [$^{14}$C] Cyanide" *J. Biol. Chem.* 256: 2162-2167, 1981.

Ishiguro, et al., "Mode of Action of Saframycin A, A Novel Heterocyclic Quinone Antibiotic. Inhibition of RNA Synthesis in Vivo and in Vitro", *Biochemistry*, 17(13): 2545-2550, 1981.

Jimeno, et al., Progress in the Acquisition of New Marine-Derived Anticancer Compounds: Development of Ecteinascidin-743 (ET-743), *Drugs Future*, 21: 1155-1165, 1996.

Kaneda, et al., "Biological Activitites of Newly Prepared Saframycins", *The Journal of Antibiotics*, XL(11): 1640-1643, 1987.

Kaneda, et al., "Antitumor Activity of New Semisynthetic Saframycin Derivatives". *Jpn. J. Cancer Res. (gann)*, 77: 1043-1049, 1986.

Kishi, et al., "Structure-Activity Relationships of Saframycins", The Journal of Antibiotics, XXXVII(8): 847-852, 1984.

Kubo, et al., "A Synthesis of the Derivatives of 1,2,3,5,10,10a-Hexahydrobrenz[f]Indolizine-6,9-Dione Having Antifungal Activity as a Simple Model of Saframycin A", *Heterocycles*, 42(1): 195-211, 1996.

Kurihara, et al., "Studies Directed Towards Total Synthesis of Saframycin: I. A Synthesis of Hexahydro-1,5-Imino-3-Benzazocin-7,10-Dione." *Tetrahedron Letters*, 23(35): 3639-3640, 1982.

Lown, et al., "Molecular Mechanisms of Binding and Single-Strand Scission of Deoxyribonucleic Acid by the Antitumor Antibiotics Saframycins A and C" *Biochemistry*, 21: 419-428, 1982.

Martinez, et al., "Phthalascidin, a Synthetic Antitumor Agent with Potency and Mode of Action Comparable to Ecteinascidin 743", *Proc. Natl Acad. Sci. USA*, 96: 3496-3501, 1999.

Martinez, et al., "Enantioselective Synthesis of Saframycin A and Evaluation of Antitumor Activity Relative to Ecteinascidin/ Saframycin Hybrids", *Organic Letters*, 1(1): 75-77, 1999.

Mikami, et al., "Blue Pigmentation of Mycelia and the Synthesis of Saframycins by Streptomyces Lavendulae", *Sixth Int. Symp. on Actinomyostee Biology*, 297-299, 1985.

Myers, et al., "Synthesis and Evaluation of Bishydroquinone Derivatives of (-)-Saframycin A: Identification of a Versatile Molecular Template Imparting Potent Antiproliferative Activity" *J. Am. Chem Soc.*, 123: 5114-5115, 2001.

Myers, et al., "A Concise, Stereocontrolled Synthesis of (-) Saframycin A by the Directed Condensation of α-Amino Aldehyde Precursors" *J. Am. Chem. Soc.* 121: 10828-10829, 1999.

Myers, et al., "Greatly Simplified Procedures for the Synthesis of α-Amino Acids by the Direct Alkylation of Pseudoephedrine Glycinamide Hydrate", *J. Org. Chem.* 64: 3322-3327, 1999.

Myers, et al., "Preparation of Chiral, C-Protected α-Amino Aldehydes of High Optical Purity and Their Use as Condensation Components in a Linear Synthesis Strategy", *J. Am. Chem. Soc.* 121: 8401-8402, 1999.

Myers, et al., "Synthesis of C-Protected α-Amino Aldehydes of High Enantiomeric Excess from Highly Epimerizable N-Protected α-Amino Aldehydes", *Organic Letters*, 2(21): 3337-3340, 2000.

Parker, et al., "Approaches to the Isoquinoline Quinone Antibiotics, Additions of an Amino Acid Derivative to a Quinone Monoacetal", *Tetrahedron Letters*, 25(33): 3543-3546, 1984.

Podhorez, D., "Stepwise Approach to the 2,3-Dihydroimidazo[1,2-a] Pyridine and 5-Oxo-1,2,3,5-Tetrahydroimidazol[1,2-a] Pyridine Ring Systems", *J. Heterocyclic Chem.* 28: 971-976, 1991.

Pospiech, et al., A New Myxococcus Xanthus Gene Cluster for the Biosynthesis of the Antibiotic Saframycin Mx1 Encoding a Peptide Synthetase, *Microbiology*, 141: 1793-1803, 1995.

Pospeich, et al., "Two Multifunctional Peptide Synthetases and an O-Methyltransferase are Involved in the Biosynthesis of the DNA-Binding Antibiotic and Antitumour Agent Saframycin Mx1 from Myxococcus Xanthus", *Microbiology*, 142: 741-746, 1996.

Rao, et al., "Mode of Action of Saframycin Antitumor Antibiotics: Sequence Selectivities in the Covalent Binding of Saframycins A and S to Deoxyribonucleic Acid" *Chem. Res. Toxicol.* 3: 262-267, 1990.

Rao, et al., "DNA Sequence Selectivities in the Covalent Bonding of Antibiotic Saframycins Mx1, Mx3, A, and S Deduced from MPE-Fe(II) Footprinting and Exonuclease III Stop Assays", *Biochemistry*, 31: 12076-12082, 1992.

Reiners, W., "Saframycins, Renieramycins, and Safracins", *The Chemistry of Ant. Antibiotics*, 2: 93-119, 1988.

Rinehart, et al., "Bioactive Compounds From Aquatic and Terrestrial Sources" *Journal of Natural Products*, 53:771-792, 1990.

Saito, et al.,"Synthesis of Saframycins. X.$^{1)}$ Transformation of (-) Saframycin A to (-) Saframycin Mx Type Compound with the Structure Proposed for Saframycin E". *Chem. Pharm. Bull.* 43: 777-782, 1995.

Saito, et al., Synthesis of Saframycins. V. Selenium Oxide Oxidation of Hexahydro-1,5-Imuno-3-Benzazocin-7,10-Dione; A Useful Method for Constructing Saframycins C and D From Saframucin B.[1], *Tetrahedron*, 46(23): 7711-7728, 1990.

Saito, et al., "Synthesis of Saframycins. XII.[1] Total Synthesis of (-)-N-Acetylsaframycin Mx 2 and Its epi-(+)-Enantiomer", *Tetrahedron*, 51: 8231-8246, 1995.

Saito, et al., "Synthesis of Saframycins. VIII.[1]) Synthesis of the ABC Ring of Safracins", *Chem. Pharm. Bull.* 40(10): 2620-2626, 1992.

Saito, et al., "Synthesis of Saframycins. VII. The Synthesis of Novel Renieramycin Congeners", *Heterocycles*, 32(6): 1203-1214, 1991.

Saito, et al., "Synthesis of Saframycins. 3. Preparation of a Key Tricyclic Lactam Intermediate to Saframycin A", *J. Org. Chem.* 54: 5391-5395, 1989.

Sakai, et al., "Additional Antitumor Ecteinascidins from a Caribbean Tunicate: Crystal Structures and Activities *in vivo*" *Proc. Natl. Acad. Sci. USA*, 89: 11456-11460, 1992.

Shawe, et al., "Saframycin Synthetic Studies", *Tetrahedron*, 47(3): 5643-5666, 1991.

Taamma, et al., "Phase I and Pharmacokinetic Study of Ecteinascidin-743, a New Marine Compound, Administered as a 24-Hour Continuous Infusion in Patients with Solid Tumors" *J. Clin. Oncol.* 19: 1256-1265, 2001.

Takahashi, K., "New Antibiotics, Saframycins A, B, C, D and E" The Journal of Antibiotics, XXX(11): 1015-1018, 1977.

Yazawa, et al., "Isolation and Structural Elucidation of New Saframycins Y3, Yd-1, Yd-2, Ad-1, Y2b and Y2b-d", *The Journal of Antiobiotics*, XXXIX(12): 1639-1650, 1986.

Zhou, et al., "Synthetic Explorations in the Saframycin-Ecteinascidin Series: Construction of Majo Chiral Subunits Through Catalytic Asymmetric Induction", *Tetrahedron Letters*, 41: 2039-2042, 2000.

Zhou, et al., "A Novel Face Specific Mannich Closure Providing Access to the Saframycin-Ecteinascidin Series of Piperazine Based Alkaloids", *Tetrahedron Letters*, 41: 2043-2046, 2000.

\* cited by examiner

ASSAY FOR IDENTIFYING BIOLOGICAL TARGETS OF POLYNUCLEOTIDE-BINDING COMPOUNDS

GOVERNMENT SUPPORT

The work described herein was supported, in part, by a grant from the National Institutes of Health (R37 CA047148). The United States government may have certain rights in the invention.

BACKGROUND OF THE INVENTION

The saframycins, isolated in the late 1970s, are a family of microbial fermentation products with significant antiproliferative activity and anti-microbial activity against gram-positive bacteria (Arai, T.; Kubo, A. In *The Alkaloids*; Brossi, A., Ed.; Academic Press: New York, 1983; Vol. 21, Chapter 3; Arai, T.; Takahashi, K. *the Journal of Antibiotics* 1977, 30, 1015–1018). Several saframycin analogues have been isolated and characterized in recent years (see, e.g., DE 2839668; U.S. Pat. No. 4,248,863; U.S. Pat. No. 4,372,947; U.S. Pat. No. 5,023,184; U.S. Pat. No. 4,837,149; and EP 329606; each of which is incorporated herein by reference). For example, saframycins A-H, R, and S have been isolated from the culture broths of *Streptomyces lavendulae*, and saframycins $M_{x1}$ and $M_{x2}$, have been isolated from the culture broths of the myxobacterium, *Myxococcus xanthus*, each of the saframycins varying in the oxidation state of the ring system and in substitution of the core structure (Saito et al. *Chem. Pharm. Bull.* 43:777, 1995). Certain saframycins, namely A and C, exhibit extreme cytotoxicity toward cultured cells and toward several experimental tumor cell lines including leukemias L1210 and P388 and Ehrlich carcinoma (Arai, T.; Mikami, Y.; Okamoto, K.; Tokita, H.; Teras, K. In *Advances in cancer chemotherapy*; University Park Press, Baltimore, 1978, 235–251; Arai, T.; Takahashi, K.; Ishiguro, K.; Mikami, Y. *Gann* 1980, 71, 790–796; Ishiguro, K.; Sakiyami, Takahashi, K.; Arai, T. *Biochemistry* 1981, 17, 2545–2550; Arai, T.; Takahashi, K.; Nakahara, S.; Kubo, A. *Experientia* 1980, 36, 1025–1027; Myers, A. G.; Plowright, A. T. *J. Am. Chem. Soc.* 2001, 123, 5114; Martinez, E.; Owa, T.; Schreiber, S. L.; Corey, E. J. *Proc. Natl. Acad. Sci. USA* 1999, 96, 3496–3501).

Saframycin A (SafA), the most potent member of this series, exhibits wide spectrum anti-cancer activity against Ehrlich ascites tumor, B16 melanoma, and murine leukemias P388 and L1210 (Arai, T.; Mikami, Y.; Okamoto, K.; Tokita, H.; Teras, K. In *Advances in cancer chemotherapy*; University Park Press, Baltimore, 1978; pp 235–251; Arai, T.; Takahashi, K.; Ishiguro, K.; Mikami, Y. *Gann* 1980, 71, 790–796; Ishiguro, K.; Sakiyami, Takahashi, K.; Arai, T. *Biochemistry* 1981, 17, 2545–2550; Arai, T.; Takahashi, K.; Nakahara, S.; Kubo, A. *Experientia* 1980, 36, 1025–1027). A structurally related class of non-quinoid natural products, the ecteinascidins, was found to possess an even more potent antiproliferative activity (Rinehart, K. L.; Holt, T. G.; Fregeau, N. L.; Keifer, P. A.; Wilson, G. R.; Perun, T. J.; Sakai, R.; Thompson, A. G.; Stroh, J. G.; Shield, L. S.; Seigler, D. S.; Li, L. H.; Martin, D. G.; Grimmelikhuijzen, C. J. P.; Gäde, G. *Journal of Natural Products* 1990, 53, 771–792; Sakai, R.; Rinehart, K.; Guan, Y.; Wang, A. H. J. *Proc. Natl. Acad. Sci. USA* 1992, 89, 11456–11460). One member of the class, ecteinascidin 743 (Et-743), has advanced to Phase III clinical trials, and it was found to be particularly active against soft tissue sarcomas without obvious toxicity (Jimeno, J. M.; Faircloth, G.; Cameron, L.; Meely, K.; Vega, E. Gomez, A.; Sousa-Faro, J. M. F.; *Drugs Future* 1996, 21, 1155–1165; Bowman, A.; Twelves, C.; Hoekman, K.; Simpson, A.; Smyth, J.; Vermorken, J.; Hoppener, F.; Beijnen, J.; Vega, E.; Jimeno, J. Hanauske, A. R. *Ann. Oncol.* 1998, 9 (*Suppl.* 2), 119; Taamma, A.; Misset, J. L.; Riofrio, M. Guzman, C.; Brain, E.; LopezLazaro, L.; Rosing, H.; Jimeno, J. M.; Cvitkovi, E. *J. Clin. Oncol.* 2001, 19, 1256–1265). By employing an efficient synthetic route to SafA, a number of saframycin structural analogues have been prepared (see U.S. Ser. No. 10/011,466, filed Nov. 5, 2001; U.S. Ser. No. 60/245,888, filed Nov. 3, 2000; each of which is incorporated herein by reference). The most active analogue, the quinaldic acid analogue of SafA (QAD), possesses nearly 30-fold greater activity than SafA in a lung carcinoma cell line and 4-fold greater activity in a melanoma cell line. QAD has been reported to show 100-fold greater potency in three human sarcoma cell lines as compared to Et-743 (Myers, A. G.; Kung, D. W., *J. Am. Chem. Soc.* 1999, 121, 10828–10829; Myers, A. G.; Plowright, A. T. *J. Am. Chem. Soc.* 2001, 123, 5114–5115).

TABLE 1

IC$_{50}$s in Tumor Cell Lines

| Compound | A375 melanoma | A549 lung carcinoma |
|---|---|---|
| (−)-Saframycin A | 5.3 nM | 133 nM |
| QAD | 1.2 nM | 4.4 nM |
| Ecteinascidin 743 | 0.15 nM | 1.0 nM |

Saframycin A has been shown to block RNA synthesis in cultured cells, and it has been suggested that saframycins A and C exhibit this potency because of their ability to bind covalently to DNA (for a discussion of the biological activity of the saframycins see, for example, Lown et al. *Biochemistry,* 1982, 21, 419; Ishiguro et al. *Biochemistry,* 1978, 17, 2545; Rao et al. *Chem. Res. Toxicol.,* 1990, 3, 262, 1990; Ishiguro et al. *J. Biol. Chem.,* 1981, 256, 2162).

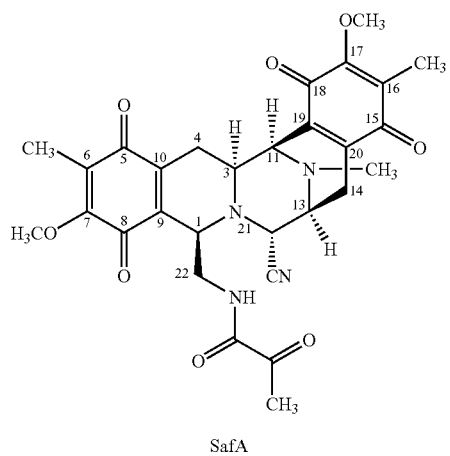

SafA

-continued

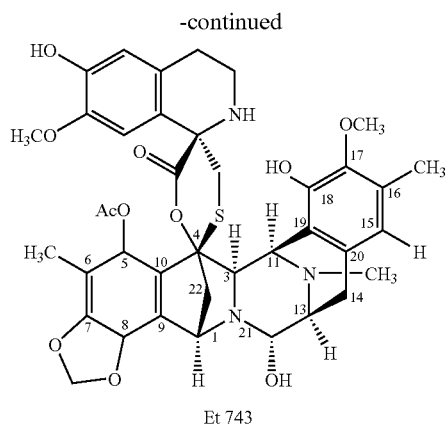

Et 743

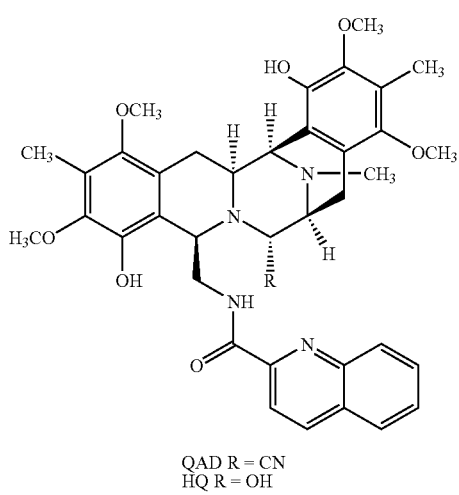

QAD R = CN
HQ R = OH

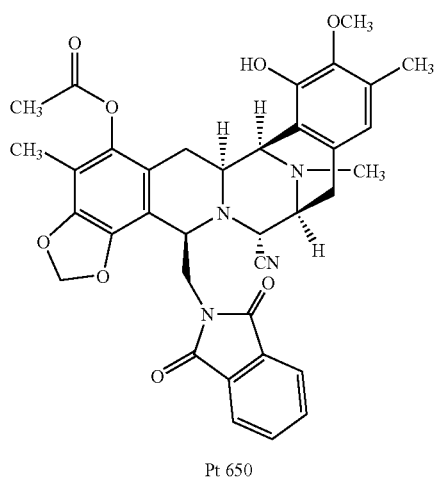

Pt 650

-continued

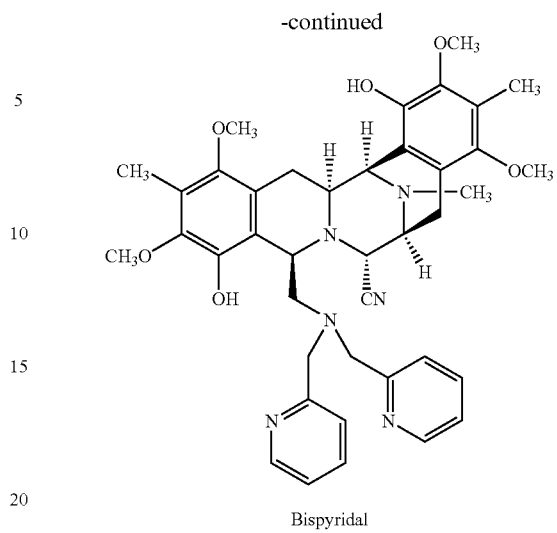

Bispyridal

Due to the potent antiproliferative activity of the ecteinascidins, saframycins, and related analogues, elucidating their biological mode of action has been an area of active research ever since their discovery. Elucidating the biological target of the saframycins may lead to the development of assays which can be used to identify better pharmaceutical agents with the same mode of action as the saframycins. Also, since many other anti-proliferative agents are known to bind DNA, an activity which is believed to be central to their biological activities, the assays developed for use with saframycins may be applicable to other DNA-binding agents.

SUMMARY OF THE INVENTION

The present invention stems from the recognition that some anti-proliferative agents exert their effects on cells by binding to nuclear DNA, thereby forming a binary complex, which is then recognized by a cellular target. This recognition event may take the form of a DNA-repair enzyme that repairs the lesion or it may lead to a signaling event that initiates apoptosis (or both). Glyceraldehyde 3-phosphate dehydrogenase (GAPDH) has been found to be the cellular target of the saframycin A/dsDNA binary complex (see Examples below). Saframycin A has been shown to bind in the minor groove of DNA in a sequence-selective manner, and to alkylate the N2 position of guanine through an imminium ion intermediate generated from the elimination of a cyano or hydroxyl group at C21 of saframycin A (FIG. 1) (Arai, T.; Mikami, Y.; Okamoto, K.; Tokita, H.; Teras, K. In *Advances in cancer chemotherapy*; University Park Press, Baltimore, 1978; pp 235–251; Arai, T.; Takahashi, K.; Ishiguro, K.; Mikami, Y. *Gann* 1980, 71, 790–796; Ishiguro, K.; Sakiyami, Takahashi, K.; Arai, T. *Biochemistry* 1981, 17, 2545–2550; Arai, T.; Takahashi, K.; Nakahara, S.; Kubo, A. *Experientia* 1980, 36, 1025–1027; Lown et al. *Biochemistry* 1982, 21, 419). The resulting binary complex then interacts with GAPDH to mediate the lethality of saframycin A within the cell. Saframycin A, the quinaldic acid analogue (QAD), and ecteinascidin 743 all are found to target cellular GAPDH and thus are believed to have a common biological mechanism of action.

In one aspect, the present invention provides a novel method of identifying the biological target of a DNA-binding agent. The method includes the formation of a binary complex of the polynucleotide and agent on a solid support such as a resin. The interaction between polynucleotide and agent is preferably covalent; however, the covalent interaction may be reversible. Either the polynucleotide or the agent may be attached directly to the solid support; however, preferably the polynucleotide is directly linked to the solid support through techniques known in the art. Once the binary complex is formed, it can be used to locate by affinity chromatography the biological target in a cell lysate, extracellular fluid, serum, plasma, blood, or any other solution or suspension which may be thought to contain the biological target. Once the ternary complex of agent, polynucleotide, and biological target has been formed on the solid support, the solid support with ternary complex attached is washed to remove non-binding proteins and cellular debris. The biological target can then be isolated and identified using various techniques in the field of protein biochemistry including SDS-polyacrylamide gel electrophoresis, silver staining, antibody binding, and/or protein microsequencing by mass spectroscopy. This novel method was used to successfully identify GAPDH as the cellular target of the saframycin A/dsDNA binary complex. The present invention also includes kits containing the reagents useful in the method of identifying a biological target. These kits may include saframycin A, saframycin analogues, ecteinascidin, ecteinascidin analogues, GAPDH protein, polynucleotides, cell lines, media, buffers, reagents, affinity resins, gels, nitrocellulose filters, vials, instruction manuals, etc., which may be useful in the practice of the inventive method.

In another aspect, the present invention provides a method of identifying compounds with a known mechanism of action. In certain embodiments, the method allows for the identification of compounds with a greater affinity for the biological target as compared to a known agent. For example, having identified the target of saframycin A as GAPDH, the inventive method can be used to identify other compounds which also target GAPDH. A polynucleotide sequence is attached to the wells of a multi-well plate. In each well is then delivered a test compound. The compound is allowed to react and form a binary complex with the attached polynucleotide. A solution of GAPDH or cell lysate is then added to each well, and the amount of GAPDH bound by the test compound/polnucleotide binary complex is quantitated for comparison to other GAPDH-targeting compounds such as saframycin A, QAD, ecteinascidin 743, and phthalascidin. The amount of GAPDH bound by the binary complex may be quantitated by any known method including immunochemistry, SDS-PAGE followed by visualization with silver staining or Coomassie Blue staining, Western blot, fluorescence, chemiluminescence, capillary electrophoresis, etc. Compounds such as saframycin A, QAD, ecteinascidin 743, and phthalascidin may be used as positive controls in determining the amount of GAPDH bound. Compounds known to not target GAPDH, such as mitomycin C and cis-platin, may be used as negative controls. Compounds identified using the inventive method for screening may be further characterized using southwestern blotting, capillary electrophoresis, affinity chromatography, competition studies, siRNA studies, GAPDH translocation studies, in vitro cytotoxicity studies, in vivo animal model studies, etc.

The method of identifying compounds targeting GAPDH is amenable to high-throughput screening techniques including robotic assisted fluid delivery, combinatorial chemistry, microfluidics, and computer analysis of the resulting data. In certain embodiments, a collection of compounds such as a combinatorial library may be provided for screening. In other embodiments, a historical collection of chemical compounds from a pharmaceutical company may screened using the inventive method. All compounds identified using the inventive method are within the scope of the present invention as well as methods of treating a proliferative disease such as cancer and other neoplasms using the identified compounds.

In another aspect, the present invention provides kits with conveniently packaged materials needed to perform the inventive methods. The kits may include polynucleotides, affinity resins, chemical compounds (such as saframycin A, ecteinascidin 743, cis-platin, trans-platin, etc.) with known targets or mechanisms of action, buffers, reagents, purified proteins such as GAPDH, antibodies useful in detecting biological targets, cell lines, cell lysates, polyacrylamide gels, vials, multi-well plates, radioisotopes, software for high-throughput screening and statistical analysis, instruction manuals, etc. For example, a kit for screening chemical compounds or small molecules to identify compounds targeting GAPDH may include polynucleotides optionally bound to a solid support, saframycin A as a positive control, mitomycin C or cis-platin as a negative control, purified GAPDH, antibodies directed to GAPDH, and an instruction manual. The kit may also contain various buffers and reagents useful in the practice of the screening method. Preferably, the materials are conveniently packaged in aliquots useful in the practice of the inventive methods and/or useful in high throughput screening with robotic equipment for fluid delivery.

The inventive methods and systems are not only useful in identifying compounds targeting GAPDH like saframycin A and ecteinascidin 743, but they may also be used to identify the targets of other agents and compounds with similar activity. For example, cis-platinated DNA has previously been found to bind HMG1. Therefore, the inventive methods could be used to identify compounds which bind DNA and the resulting binary complex targets HMG1. Other DNA binding agents useful in the inventive screening methods include topoisomerase poisons, e.g., camptothecin (and its analogs) and quinolone, which are known to target DNA topoisomerase II.

BRIEF DESCRIPTION OF THE DRAWING

FIG. 5 depicts the Southwestern blot technique using GAPDH and saframycins.

FIG. 8A shows GAPDH expression levels as determined by Western blot analysis. FIG. 8B shows $GI_{50}$ of cis-platin in A549 tumor cells unchanged when treated with GAPDH siRNA (left) and $GI_{50}$ of QAD in A549 tumor cells increased approximately 9-fold when treated with GAPDH siRNA (right).

DEFINITIONS

Figure 1A:
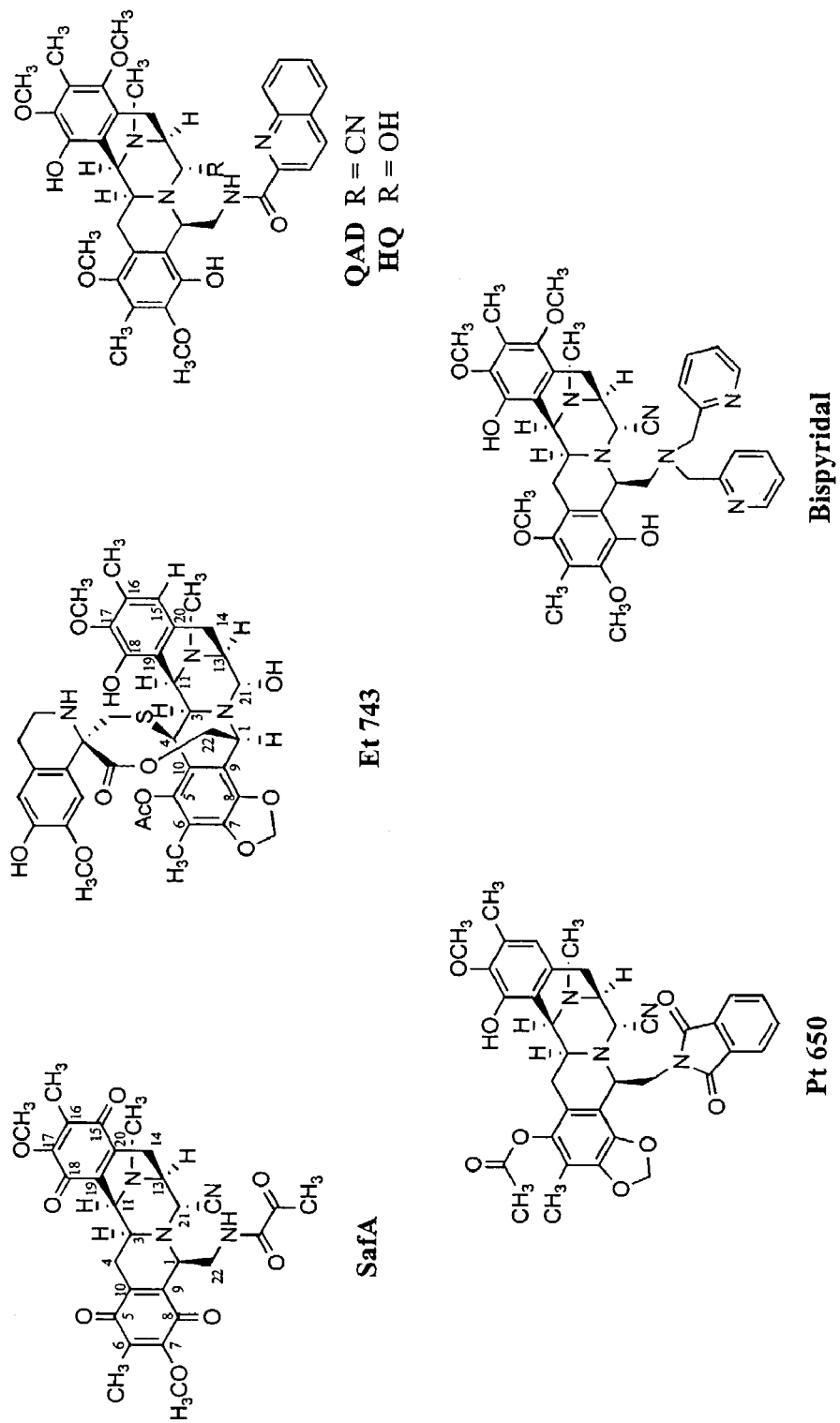
FIG. 1A shows the structure of (−)-saframycin A (SafA); ecteinascidin 743 (Et 743); the quinaldic acid analogues of (−)-saframycin A, QAD R=CN, HQ R=OH; phthalascidin (Pt 650), an analogues of ecteinascidin 743; bispyridal, an inactive analogue of saframycin A.

A chemical compound or compound as used herein can include organometallic compounds, organic compounds, inorganic compounds, metals, transitional metal complexes, and small molecules. In certain preferred embodiments, polynucleotides are excluded from the definition of compounds. In other preferred embodiments, polynucleotides and peptides are excluded from the definition of compounds. In a particularly preferred embodiment, the term compounds refers to small molecules (e.g., preferably, non-peptidic and non-oligomeric) and excludes peptides, polynucleotides, transition metal complexes, metals, and organometallic compounds.

A drug or drug candidate may include any chemical compound used in the clinic or to be used in the clinic for the treatment or prevention of a disease or condition. In certain embodiments, the drug or drug candidate is a small molecule. In other embodiments, the drug or drug candidate is a protein or peptide. In other embodiments, the drug or drug candidate is a polynucleotide. In certain embodiments, a drug or drug candidate is any pharmaceutical agent that has been approved by the Food and Drug Administration (FDA) for the treatment of a disease. A drug candidate may be in pre-clinical or clinical testing, and it may not be approved by the Food and Drug Administration but may be in the process of receiving FDA approval. For example, drugs for human use listed by the FDA under 21 C.F.R. §§ 330.5, 331 through 361; 440–460, and drugs for veterinary use listed by the FDA under 21 C.F.R. §§ 500–582, incorporated herein by reference, are all considered drugs in the present invention. For a more comprehensive discussion of drugs and drug candidates, see Goodman & Gilman's *The Pharmacological Basis of Therapeutics*, Ninth Ed., McGraw-Hill, 1996; *The Merck Index*, Eleventh Ed., 1989; *The Merck Manual*, Seventeenth Ed. 1999; the entire contents of each of which are hereby incorporated by reference. In certain preferred embodiments, a drug is an anti-neoplastic agent. In other embodiments, a drug is an antibiotic.

Natural product-like compounds are compounds that are similar to complex natural products which nature has selected through evolution. Typically, these compounds contain one or more stereocenters, a high density and diversity of functionality, and a diverse selection of atoms within one structure. In this context, diversity of functionality can be defined as varying the topology, charge, size, hydrophilicity, hydrophobicity, and reactivity to name a few, of the functional groups present in the compounds. The term, "high density of functionality", as used herein, can preferably be used to define any molecule that contains preferably three or more latent or active diversifiable functional moieties. These structural characteristics may additionally render the inventive compounds functionally reminiscent of complex natural products, in that they may interact specifically with a particular biological target, and thus may also be functionally natural product-like.

A peptide or protein comprises a string of at least three amino acids linked together by peptide (amide) bonds. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

Small molecule refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon—carbon bonds, and has a molecular weight of less than 1500, although this characterization is not intended to be limiting for the purposes of the present invention. Examples of small molecules that occur in nature include, but are not limited to, taxol, dynemicin, and rapamycin. In certain other preferred embodiments, natural-product-like small molecules are utilized.

The term substituted, in general, whether preceded by the term "optionally" or not, and substituents contained in formulas of this invention refer to the replacement of hydrogen radicals in a given structure with the radical of a specified substituent. It will be appreciated that the compounds, as described herein, may be substituted with any number of substituents or functional moieties. When more than one position in any given structure may be substituted with more than one substituent selected from a specified group, the substituent may be either the same or different at every position. As used herein, the term substituted is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer.

A target is a biological molecule that binds an agent or complex so that a biological effect occurs. In certain embodiments, the target is a protein that binds a small molecule or drug alone or a small molecule (drug)/polynucleotide complex thereby mediating the effect of the drug. This interaction may directly cause the observed biological effect of the drug, or it may indirectly cause the observed biological effect through a series of interactions with other biological molecules. In certain embodiments, the target is a cellular protein. In other embodiments, the target is a nuclear protein. In other embodiments, the target is an extracellular protein. For example, the target of the saframycin A/dsDNA complex is GAPDH, and the target of the cis-platin/dsDNA complex is HMG1. In certain embodiments, the target is a polynucleotide which may include a particular sequence of nucleotides recognized by the agent or drug.

DETAILED DESCRIPTION OF PREFERRED EMBODIMENTS

The present invention provides methods and systems of identifying biological targets of chemical compounds as well as methods and systems of identifying chemical compounds which target a particular protein. The methods and systems of the present invention stem from the recognition that a ternary complex comprising a polynucleotide, a small molecule, and a biological target is formed as part of the mechanism of action of many small molecules that bind a polynucleotide to cause their biological effect. In particular, glyceraldehyde 3-phosphate dehydrogenase (GAPDH) has been discovered to recognize and bind the binary complex formed between saframycin A and dsDNA. The resulting ternary complex comprising GAPDH, saframycin A, and dsDNA has been found to play a role in the cytotoxicity of saframycin A and its analogues. In the present invention, this recognition of the formation of a ternary complex has led to the development of methods of identifying the biological target of other binary complexes involving a small molecule and a polynucleotide and methods of screening for other compounds with a similar mechanism of action as saframycin A.

Small Molecule

Any small molecule that binds a polynucleotide such that the resulting small molecule/polynucleotide complex is recognized by a biological target (e.g., a protein) to form a ternary complex may be useful in the present invention. Many small molecules are known or are thought to bind a polynucleotide such as DNA as part of their mechanism of action in causing their biological effect. Molecules that have been described in the literature as binding DNA include nitrogen mustards (e.g., mechlorethamine, cyclophosphamide, melphalan, chlorambucil), nitrosoureas (e.g., BCNU, CCNU, methyl-CCNU), alkyl sulfonates (e.g., busulfan), platinum compounds (e.g., cis-platin), anthracyclines (e.g., doxorubicin, daunorubicin, adriamycin, menogaril), bleomycin, anthramycins, tomaymycin, quinocarcin, DX-52, cyanocycline, lemonomycin, naphthyridinomycin, carzinostatin, duocarmycins, CC-1065, and pyrindamycin. The complex formed between the small molecule and the polynucleotide may be covalent or non-covalent; preferably, the interaction is covalent. The covalent interaction may be reversible or non-reversible. The binary complex formed between the polynucleotide and small molecule is then recognized by a biological target which either directly or indirectly causes the biological effect of the small molecule on a living system such as a cell, tissue, organ, or organism.

In certain embodiments, the small molecules of the present invention are non-polymeric, non-oligomeric, and non-peptidic. In certain embodiments, the small molecules used in the present invention are drugs or drug candidates. In certain other embodiments, the molecular weights of the small molecules of the present invention may range from 100 g/mol to 5,000 g/mol, preferably from 200 g/mol to 2,000 g/mol. These molecules may contain numerous carbon—carbon bonds and possess a high degree of functionality. The small molecules may also contain one or more (or numerous) stereocenters. In some embodiments, the small molecules are natural products first isolated from organism such as plants, sea creatures, fungi, or bacteria. In other embodiments, the small molecules are prepared by synthetic methods in the laboratory based on natural products produced by Nature. In still other embodiments, the small molecules are analogues or derivatives of natural products and have been prepared in the laboratory.

Any collection of small molecules may be screened using the inventive methods. The small molecules may be natural or synthesized in the laboratory. In some particular embodiments, the collection of small molecules may comprise compounds that are structurally related to one another, e.g., are analogs of one another and/or of a common parent compound. In other embodiments, the small molecules screened using the inventive methods may be provided as a combinatorial library prepared by technologies and methods known in the field of combinatorial chemistry.

In certain embodiments, the small molecules of the present invention are molecules that form a binary complex with dsDNA and the resulting binary complex is recognized by GAPDH. In certain preferred embodiments, the small molecules are saframycin A, ecteinascidin 743, phthalascidin, or other derivatives of these natural products such as those described in U.S. Ser. No. 10/011,466, filed Nov. 5, 2001, and U.S. Ser. No. 60/245,888, filed Nov. 3, 2000, each of which is incorporated herein by reference. Saframycin A as well as some of its synthetic analogues are particularly useful in the present invention. In some instances, an analogue with a greater or lesser effect than saframycin A is used in the inventive assay. In certain embodiments such as when a more potent compound is being screened for, saframycin A or a potent analogue such as QAD is used in the inventive assay to bind DNA and form a binary complex. As described above, saframycin A or its analogues may be obtained from natural sources, or they may be prepared synthetically or semi-synthetically in the laboratory. As would be appreciated by one of skill in the art, certain analogues that do not appear in Nature must be prepared synthetically in the laboratory. In certain embodiments, these analogues are prepared by de novo synthesis, and in other embodiments, a natural product is isolated and derivatized or modified to yield the desired analogues.

In certain preferred embodiments, the saframycin analogues have the structure:

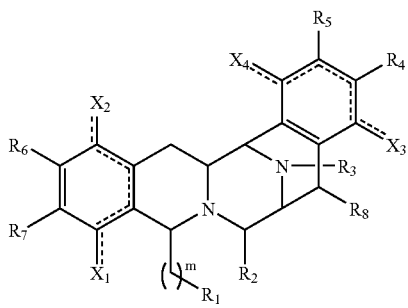

wherein $R_1$ is $NR_AR_B$, $-OR_A$, $-SR_A$, $-C(=O)R_A$, $-C(=S)R_A$, $-S(O)_2R_A$, or an aliphatic, heteroaliphatic, aryl, heteroaryl, (aliphatic)aryl, (aliphatic)heteroaryl, (heteroaliphatic)aryl, or (heteroaliphatic)heteroaryl moiety, wherein each occurrence of $R_A$ and $R_B$ is independently hydrogen, $-(C=O)R_C$, $-NHR_C$, $-(SO_2)R_C$, $-OR_C$, or an aliphatic, heteroaliphatic, aryl, or heteroaryl moiety, or $R_A$ and $R_B$, when taken together form an aryl, heteroaryl, cycloaliphatic, or cycloheteroaliphatic moiety, wherein each occurrence of $R_C$ is independently hydrogen, $-OR_D$, $-SR_D$, $-NHR_D$, $-(C=O)R_D$, or an aliphatic, heteroaliphatic, aryl, or heteroaryl moiety, wherein each occurrence of $R_D$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein $R_2$ is hydrogen, $-OR_E$, $=O$, $-C(=O)R_E$, $-CO_2R_E$, $-CN$, $-SCN$, halogen, $-SR_E$, $-SOR_E$, $-SO_2R_E$, $-NO_2$, $-N(R_E)_2$, $-NHC(O)R_E$, or an aliphatic, heteroaliphatic, aryl, or heteroaryl moiety, wherein each occurrence of $R_E$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein $R_3$ is hydrogen, a nitrogen protecting group, $-COOR_F$, $-COR_F$, $-CN$, or an aliphatic, heteroaliphatic, aryl, or heteroaryl moiety, wherein each occurrence of $R_F$ is independently hydrogen, a protecting group, or an aliphatic, heteroaliphatic, aryl, heteroaryl, alkoxy, aryloxy, alkylthio, arylthio, heteroaryloxy, or heteroarylthio moiety;

wherein $R_4$ and $R_6$ are each independently hydrogen, or an aliphatic, heteroaliphatic, aryl, heteroaryl, acyl, alkoxy, aryloxy, alkylthio, arylthio, heteroaryloxy, or heteroarylthio moiety;

wherein $R_5$ and $R_7$ are each independently hydrogen, $-OR_G$, $-C(=O)R_G$, $-CO_2R_G$, $-CN$, $-SCN$, halogen, $-SR_G$, $-SOR_G$, $-SO_2R_G$, $-NO_2$, $-N(R_G)_2$, $-NHC(O)R_G$, or an aliphatic, heteroaliphatic, aryl or heteroaryl moiety, wherein each occurrence of $R_G$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

wherein $R_8$ is hydrogen, alkyl, $-OH$, protected hydroxyl, $=O$, $-CN$, $-SCN$, halogen, $-SH$, protected thio, alkoxy, thioalkyl, amino, protected amino, or alkylamino;

wherein m is 0–5;

wherein $X_1$, $X_2$, $X_3$ and $X_4$ are each independently hydrogen, $-OR_H$, $=O$, $-C(=O)R_H$, $-CO_2R_H$, $-CN$, $-SCN$, halogen, $-SR_H$, $-SOR_H$, $-SO_2R_H$, $-NO_2$, $-N(R_H)_2$, $-NHC(O)R_H$, or an aliphatic, heteroaliphatic, aryl, or heteroaryl moiety, wherein each occurrence of $R_H$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;

whereby if at least either $X_1$ and $X_2$ or $X_3$ and $X_4$ are doubly bonded to the 6-membered ring, then the dotted bonds in either or both of the 6-membered rings represent two single bonds and one double bond, and a quinone moiety is generated, or if at least either $X_1$ and $X_2$ or $X_3$ and $X_4$ are singly bonded to the 6-membered ring, then the dotted bonds in either or both of the 6-membered rings represent two double bonds and one single bond, and a hydroquinone moiety is generated;

whereby each of the foregoing aliphatic, heteroaliphatic and alkyl moieties may independently be substituted or unsubstituted, branched or unbranched, or cyclic or acyclic, and each of the foregoing aryl or heteroaryl moieties may independently be substituted or unsubstituted.

Polynucleotide

The polynucleotide used in the inventive system or methods may be any polynucleotide found to interact with a small molecule of interest. In certain embodiments, the particular polynucleotides useful in any given embodiment of the present invention will depend on the small molecule being used in that embodiment. For example, in certain embodiments the small molecule is known or is demonstrated to bind DNA; therefore, DNA is used as part of the assay. DNA may be used in a double-stranded or single-stranded form; preferably, the DNA is double-stranded. In other embodiments, RNA may be used in the inventive system or methods. RNA molecules may be used in the invention to identify small molecules that bind to RNA and interact with ribosomes or other proteins that operate on RNA. Preferably, the RNA is single-stranded, though it may be double-stranded, or folded into a three-dimensional conformation. In other embodiments, a hybrid of DNA and RNA may be used in the invention. In certain embodiments, a synthetic analogue of DNA or RNA is used in the invention, for example, DNA made with phosphothioate linkages rather than phosphodiester linkages. In other embodiments, a chemically modified polynucleotide molecule is used, for example, methylated DNA. As would be appreciated by one of skill in the art, the polynucleotide useful in the present invention depends on the small molecule being studied.

The polynucleotide may be provided in a linear, circular, super-coiled, etc. form. For instance, a super-coiled DNA plasmid may be attached to a solid support and used in the inventive method to identify small molecules that interact with DNA and target Topisomerase I or Topoisomerase II. DNA may be provided as chromosomal or mitochondrial DNA. RNA may be provided as mRNA, tRNA, or rRNA. The polynucleotide may be provided as a synthetic oligomer, a viral DNA, a viral RNA, a plasmid, a cosmid, a yeast artificial chromosome, chromosome, etc. The length of the polynucleotide may range from 10 bases to 100 kb, preferably from 10 bases to 1 kb. In certain preferred embodiments, the polynucleotide is provided as a synthetic oligomer of 10 to 500 bases or base pairs; preferably from 20 to 250 bases or base pairs; and more preferably, from 25 to 100 bases or base pairs. The polynucleotide may be provided using any methods known in the art. Method for synthesizing polynucleotides and analogues thereof are well known to those skilled in the art, examples of such synthesis can be found, for example, in U.S. Pat. Nos. 4,419,732; 4,458,066; 4,500,707; 4,668,777; 4,973,679; 5,278,302; 5,153,319; 5,580,969; 5,652,355; 5,786,461; 5,773,571; 5,539,082; 5,476,925; 5,939,273; 5,646,260; and 6,258,539, each of which in incorporated herein by reference. For example, a DNA oligomer may be prepared on a DNA synthesizer. The DNA may also be provided as a restriction fragment resulting from a larger piece of DNA being cut with a restriction endonuclease and optionally purified. RNA molecules may also be synthesized using a RNA synthesizer, or RNA molecules may be prepared by in vitro or in vivo transcription of a DNA template. The desired RNA molecule may then be optionally purified. In certain preferred embodiments, the polynucleotide is attached to a solid support such as a surface or a polymeric bead using chemistry known in the art. In certain embodiments, the polynucleotide is attached to a glass slide. In other embodiments, the polynucleotide is attached to the bottom of a well of a multi-well plate. In certain embodiments, the polynucleotide is attached to the solid support through a linker of non-specific bases.

Depending on the small molecules being used in the invention, the polynucleotide may include a particular recognition sequence. For example, many small molecules that bind DNA or RNA have particular recognition sequences where the small molecule has been found to bind with a certain degree of affinity and specificity. In certain embodiments, a polynucleotide may include at least one recognition sequence. In other embodiments, a polynucleotide may contain more than one recognition sequence so that more than one small molecule will bind to the polynucleotide. In certain embodiments, the recognition sequence is less than 30 bases, preferably less than 20 bases, and more preferably less than 10 bases. In certain embodiment, for example with saframycin A, the recognition sequence is only 3 base pair long. Saframycin A has been found bind to dsDNA that is G-rich. In particular, any three base pair motif containing G, with the sequences 5'-GGG-3' and 5'-GGPy-3' being preferred, may be used in the inventive method and system. In preparing the polynucleotide for use in a system using a particular small molecule, it is useful to determine the recognition sequence of the small molecule by researching the literature or determining the recognition sequence by any of the methods known in the art such as DNA foot-printing, DNA sequencing, structural studies, DNA protection experiments, etc.

Biological Target

The biological target of the small molecule/polynucleotide binary complex may be any cellular or extra-cellular biomolecule. In certain embodiments, the biological target is a cellular biomolecule such as a protein, peptide, polynucleotide, lipid, carbohydrate, etc. Depending on the small molecule, the biological target may be an extra-cellular or intra-cellular protein. In certain embodiments, the biological target is an extra-cellular protein, and in other embodiments, the biological target is an intra-cellular target. In certain particular embodiments, the biological target is a protein that is found in the nucleus or is capable of being transported into the nucleus. The protein target may be, for example, an enzyme, a structural protein, or a signaling protein.

The biological target may be provided in either purified or unpurified form. In assaying to determine the biological target of a small molecule/polynucleotide binary complex, the target may be provided as a collection of potential targets (e.g., a cell lysate). The use of a cell lysate to provide the biological target allows one to scan proteins, possible substantially all proteins, expressed in a particular cell line to find the biological target. In certain embodiments, several different cell lines including different tissues or different organisms of interest may be used to confirm the identification of the biological target. Once the biological target has been identified, it may be provided as a purified or partially purified protein depending on whether the protein is already known and has been characterized and over-expressed. If a biological target has not been identified previously, the gene of the biological target may be identified, e.g., using a partial amino acid sequence derived from microsequencing in order to further characterize and possibly clone and overexpress the biological target.

In screening for more potent chemical compounds or compounds with a similar biological target, a more purified sample of the biological target may be used or a cell lysate containing the biological target may be used. The purified biological target may be obtained from cells such as bacteria (e.g., *E. coli*), fungal (e.g., *Saccharomyces cerevisiae, Pichia pastois*), insect cells (e.g., Sf9), or mammalian cells (e.g., CHO cells) which overexpress the biological target. The purified biological target may be greater than 50% pure, greater than 75% pure, greater than 90% pure, greater than 95% pure, greater than 98% pure, greater than 99% pure, or greater than 99.9% pure. In other embodiments the biological target may be commercially available in purified form.

In certain embodiments, the biological target protein may be modified or derivatized as compared to its wild type form. For instance, the target protein may be modified to make it more amenable for use in high-throughput screening. Specific amino acid residues may be mutated, entire portions of the protein may be removed, or amino acid residues may be added. These modifications may effect solubility, stability, signal-to-noise ratios in screening, etc. In certain embodiments, the target protein may be labeled with a fluorescent marker. In certain other embodiments, the target protein may be modified to include an antibody epitope for recognition with an antibody. In still other embodiments, a tag may be added to the protein to facilitate purification of the protein. In other embodiments, the protein target may be labeled with a radioisotope such as $^{125}$I, $^{32}$P, $^{35}$S, etc.

The biological target of the saframycin A/dsDNA binary complex has been shown to be GAPDH. The GAPDH protein used in the invention may be from any species of plant, animal, fungus, or bacteria. In certain preferred embodiments, the GAPDH used in the invention is at least 80% homologous to human GAPDH, preferably the GAPDH is greater than 90% homologous, and more preferably the GAPDH is greater than 95% homologous. The amino acid sequence of GAPDH from human liver is shown below:

```
  1 mgkvkvgvng fgrigrlvtr aafnsgkvdi vaindpfidl nymvymfqyd sthgkfhgtv
 61 kaengklvin gnpitifqer dpskikwgda gaeyvvestg vfttmekaga hlqggakrvi
121 isapsadapm fvmgvnheky dnslkiisna scttnclapl akvihdnfgi veglmttvha
181 itatqktvdg psgklwrdgr galqniipas tgaakavgkv ipelngkltg mafrvptanv
241 svvdltcrle kpakyddikk vvkqasegpl kgilgytehq vvssdfnsdt hsstfdagag
301 ialndhfvkl iswydnefgy snrvvdlmah maske
```

In certain embodiments, the GAPDH protein used in screening may be provided from genetically altered organisms that have been engineered to over-express GAPDH. In other embodiments, the GAPDH protein may be provided from commercial sources such as Sigma (e.g., GAPDH from human erythrocytes (Sigma G6019), GAPDH from rabbit muscle (Sigma G0763)). The GAPDH as described above may be further modified by conjugating it to a fluorescent tag or labeling it with a radioisotope for identification and quantitation of the amount of GAPDH bound by a small molecule/polynucleotide binary complex. In other embodiments, an antibody specific for GAPDH may be used to detect and quantitate the amount of GAPDH bound by a binary complex of small molecule and polynucleotide using any of the techniques of immunochemistry. For example, the anti-GAPDH antibody may be tagged or labeled to facilitate detection and quantitation of bound antibody, or another antibody may be used to detect the presence of anti-GAPDH antibody.

Methods of Identifying a Biological Target

The present invention provides a novel method for screening and identifying a biological target of a binary complex formed between a small molecule and a polynucleotide. In identifying a biological target, it has been recognized that the biological target does not bind the small molecule or polynucleotide alone, but instead the small molecule must be bound to a polynucleotide to form a binary complex that is then recognized by the biological target. This recognition led to the inventive method for identifying a biological target using a binary complex of small molecule and ploynucleotide to fish for the biological target in a collection of proteins such as those found in a cell lysate.

In certain embodiments, the binary complex of small molecule and polynucleotide is attached through a covalent or non-covalent linkage to a solid support. Preferably, the binary complex is attached through a covalent linkage; however, a strong interaction such as an antibody-antigen interaction or a biotin-streptavidin interaction would also be suitable for attaching the binary complex to the solid support. The solid support may be any material that can be derivatized and used to attach the polynucleotide, small molecule, or a pre-formed binary complex. In certain preferred embodiments, the solid support is a resin such as AffiGel-15, AffiGel-10 (Biorad catalogue #153-6046 and 153-6052), Oligo-Affinity Resin (Glen Research, 24-4001), and Toyopearl Resin (Toso Haas, 65CBM01B). The solid support may also be a surface such as a glass or plastic surface. The solid support can also be the surfaces making up a well in a multi-well plate. The solid support can be any material that allows one to attach the binary complex, allow a biological target to bind the binary complex, wash away unbound proteins, and then identify the bound biological target. Other solid supports include magnetic beads, metal surfaces, tissue culture plates, untreated plates, etc.

In forming the binary complex on a solid support, either the polynucleotide, the small molecule, or the binary complex may be bound to the solid support. In certain embodiments, the polynucleotide is directly attached to the solid support, and the small molecule is attached indirectly through its interaction with the polynucleotide. Attaching the polynucleotide to the solid support has the advantage of being able to engineer a linker of bases between the recognition site of the polynucleotide and the solid support. Therefore, the site where the small molecule interacts with the polynucleotide is far enough away from the solid support to prevent the solid support from interfering with the binding of the small molecule. Polynucleotides of the appropriate length and sequence may be directly synthesized on an affinity resin using standard phosphoramidite chemistry and a DNA or RNA synthesizer. A second strand of DNA or RNA may be annealed to the polynucleotide attached to the solid support. Optionally, the unoccupied binding sites on the solid support are blocked, and the unbound polynculeotide or polynucleotide monomers are washed away or removed.

In other embodiments, the small molecule is directly attached to the solid support, and the polynucleotide is attached indirectly through its interaction with the small molecule. In attaching the small molecule to the solid support directly, a linker between the small molecule and the solid support may be used to provide enough space for the bound small molecules and a polynucleotide to interact. For example, AffiGel-15 matrix with its longer linker may be a preferable solid support as compared to AffiGel-10 with its shorter linker. One must also consider the site at which the small molecule is attached to the solid support because the area, surface, or functional groups of the small molecule that interact with the polynucleotide should not be hindered by a linker moiety or by the solid support. Optionally, the unoccupied binding sites on the solid support are blocked, and the unbound small molecule is washed away or removed.

Once the solid support with one of the members of the binary complex attached is formed. The other member—the small molecule if the polynucleotide is attached to the solid support, or the polynucleotide if the small molecules is attached to the solid support—is contacted with the solid support under suitable conditions to allow for the binary complex to form. The other member is preferably provided in pure or substantially pure form so as to form only the desired binary complexes. The condition for formation of the binary complex may be optimized to allow for a significant portion of the member bound to the solid support to form the binary complex. In certain embodiments, the formation of the binary complex is done under conditions close to physiological conditions since presumably these interactions are occurring in living systems. In certain embodiments, the solid support may display 0.1 to 10 nmol of the bound polynucleotide or small molecules, and the other member of the binary complex may be added to the solid support at an excess ranging from 1.1 to 1000-fold. Preferably, the binary complex is formed at a temperature ranging from 20° C. to 40° C., preferably 25° C. to 37° C., more preferably at approximately 37° C. The binary complex may be allowed to form over 1 to 30 hours, preferably 5 to 20 hours, and more preferably 10–20 hours. The pH of the mixture may range from 6.0 to 8.0, preferably from 7.0 to 8.0, and more preferably approximately 7.4. In certain embodiments, a buffered solution is used to maintain the proper pH during the formation of the binary complex. The salt concentration may also be adjusted to ensure formation of the binary complex. In certain embodiments, the salt concentration is around physiological concentration. In certain embodiments, the salt concentration is between 50–200 mM NaCl, preferably 50–150 mM NaCl, more preferably approximately 100 mM NaCl. Other salts such as KCl, $MgCl_2$, $MgCl_2$, and sodium phosphate may also be used in the reaction mixture. The formation of the binary complex may be monitored by any methods known in the art to ensure that a sufficient percentage of the bound member has been converted to the binary complex. In certain preferred embodiments greater than 80% of the bound member is converted to the binary complex, preferably greater than 90%, more preferably greater than 95%, and most preferably greater than 98%.

After the binary complex is formed on the solid support, the support with the binary complex is washed to remove any unbound materials. In certain embodiments, the washing is repeated to ensure the removal of all unbound materials. The washed binary complex bound to a solid support is then incubated with a biological target or collection of potential biological targets in order to allow a ternary complex of polynucleotide, small molecule, and biological target to form. In certain embodiments, the affinity resin is incubated with a tissue homogenate or cell lysate to allow for formation of the ternary complex; however, any solution or suspension of potential biological targets may be used in the inventive methods including serum, blood, plasma, cerebral spinal fluid, extracellular fluid, lymph, nuclear extracts, etc. In certain embodiments, the tissue or cells may be from a specific organ or species. Preferably, the tissue or cells are mammalian, more preferably human. The formation of the ternary complex is also performed under conditions close to physiological conditions as described supra. After the ternary complex has formed on the solid support, the solid support is washed to remove any unbound materials such as protein, nucleic acids, lipids, sugars, etc. Presumably at this time, the solid support has bound to it a ternary complex involving the biological target, polynucleotide, and small molecule or drug.

The biological target is then characterized to determine the identity of the biological target. The characterization may be performed using any methods known in the art, and the characterization will depend on the nature of the biological target as would be appreciated by one of skill in this art. For example, if a biological target was a polynucleotide DNA or RNA sequencing may be used to characterize the target. If the biological target is a protein, SDS-PAGE followed by microsequencing of the target protein may be used to characterize and identify the target protein. In certain preferred embodiments, the biological target is a protein. The target protein may then be released from the affinity matrix using harsh conditions such as heat denaturation. The protein may then be resolved using SDS-polyacrylamide gel electrophoresis. The band of protein can then be cut out and submitted for peptide microsequencing by Edmann degradation or mass spectrometry sequencing. The resulting amino acid sequence is then compared to a database of amino acid sequences to determine the identity of the target. In certain embodiments, the biological target may be an unknown protein, and the target may be further studied by cloning the gene encoding the target protein. Methods for cloning genes and characterizing protein are well known in the art (please see, *Molecular Cloning: A Laboratory Manual*, 2nd Ed., ed. by Sambrook, Fritsch, and Maniatis (Cold Spring Harbor Laboratory Press: 1989); *Nucleic Acid Hybridization* (B. D. Hames & S. J. Higgins eds. 1984); the treatise, *Methods in Enzymology* (Academic Press, Inc., N.Y.); *Immunochemical Methods in Cell and Molecular Biology* (Mayer and Walker, eds., Academic Press, London, 1987); Ausubel et al. *Current Protocols in Molecular Biology* (John Wiley & Sons, Inc., New York, 1999); *Transcription and Translation* (B. D. Hames & S. J. Higgins eds. 1984); *Handbook of Experimental Immunology*, Volumes I–IV (D. M. Weir and C. C. Blackwell, eds., 1986); each of which is incorporated herein by reference). The biological target may be further characterized by Southwestern blot, cell fractionation studies, confocal microscopy, gene expression inhibition studies, gene overepxression, etc.

The method of identifying a protein target may be adapted for high throughput screening of small molecules for their biological targets. For example, in one embodiment, either end of a polynucleotide is biotinylated. The biotinylated polynucleotide is then contacted with the small molecule or drug of interest so that a binary complex is formed (e.g., the polynucleotide is alkylated by the small molecule). The binary complex is then incubated with a tissue or cell lysate as described above to cause the formation of a ternary complex with the biological target. The mixture is then added to a well of a 96-well or 384-well plate, wherein each well represents a different a small molecule or durg. The wells of the plate are coated with streptavidin to pull out the biotinylated polynucleotide. Target protein attached to the biotinylated polynucleotide through an interaction with the small molecule is attached to the plate. The non-bound proteins are then washed away. The bound protein as part of a ternary complex is then analyzed by any method known in the art including SDS-PAGE, microsequencing, antibody binding assay, etc., as described above. In this way, hundreds to thousands of drug or small molecules are screened at once to identify their biological target. In certain embodiments, greater than 50 small molecules are screened in parallel, preferably greater than 100, more preferably greater than 200, and most preferably greater than 500. The high-throughput screen may be adapted for use with robotic equipment and software designed for high-throughput screening.

Method of Screening Chemical Compounds

The present invention also provides a method and system for screening collections of chemical compounds for compounds that have the same biological target. In certain embodiments, the compounds may be screened to identify those compounds that are more potent at binding the target. As described above, the chemical compound must form a binary complex with a polynucleotide that is then recognized by the biological target. Once a binary complex is formed with the test chemical compound, the biological target is added to the binary complex to determine if the biological target will bind the binary complex and optionally the extent of binding the biological target (i.e., $IC_{50}$). In certain embodiments, the inventive method is adapted for high-throughput screening of chemical compounds.

The test chemical compound is incubated with polynucleotide of the proper sequence to form a binary complex. As would be appreciated by one of skill in this art, the conditions for forming the binary complex and the nature of the polynucleotide should allow for formation of the binary complex with a control compound which will give a positive result under these conditions. In certain embodiments, the polynucleotide is attached to a solid support to allow for the removal of unwanted and unbound materials. After the binary complex has been allowed to form, the binary complex is incubated with a suspension or solution known to contain the target molecule of the positive control compound. In certain embodiments, the target is provided as a partially or substantially purified compound. In other embodiments, the target is provided as a tissue homogenate or cell lysate. Unbound proteins are washed away from the ternary complex, and the amount of the biological target bound to the binary complex is determined by any method known in the art. In certain embodiments, target protein binding is determined by colorimetric, fluorometric, or chemiluminescent determination. These methods of determination take advantage of using an antibody known to recognize the target protein to determine if the protein target has bound to the small molecule on the polynucleotide substrate and optionally to quantitate the amount of protein bound. Antibodies useful in the inventive method may be engineered to chemiluminesce, fluoresce, or emit visible wavelength light when the appropriate conditions are met or the appropriate reagents are added. In certain embodiments, engineered monoclonal antibodies directed against the target protein are used in the inventive method. This method may be used in conjunction with high-throughput screening equipment and software.

For example, if one were screening for compounds with a similar activity to saframycin A, one would use a polynucleotide capable of being alkylated by saframycin A, and the target assayed for would be GAPDH. In assaying for small molecules with a similar mode of action as saframycin A, a collection of unrelated molecules may be screened, or the screened molecules may all be derivatives of saframycin A. The polynucleotide may be designed with a G-rich region for binding saframycin A. Since the biological target of saframycin A is known to be GAPDH, a purified or partially purified solution of GAPDH may be used to provide the biological target. For detection of GAPDH bound to the binary complex of small molecule and polynucleotide, one could use an antibody known to bind GAPDH. This antibody may be engineered to provide a calorimetric, fluorometric, or chemiluminescent readout for bound GAPDH. In certain embodiments, compounds with a greater affinity for GAPDH may be desired. In other embodiments, any compound that targets GAPDH may be desired. The compounds identified by the inventive screening methods may be used as pharmaceutical agents in the treatment of proliferative disorders such as cancer, benign growths, etc. The identified compounds may also be used as lead compounds in the development of novel therapeutic agents in the treatment of proliferative disorders. The compounds identified may also be used as antimicrobial agents.

In certain embodiments, a competitive ligand is used in an assay as a selection criterion for the binding of the small molecule/DNA binary complex to the biological target. The competitive binding of another binary complex allows one to select for more potent drugs, which have a greater affinity for the target protein than the small molecule of the competitive ligand. In this competitive assay, a polynucleotide/small molecule complex of known binding affinity for the biological target is prepared. In certain embodiments, the complex is prepared by mixing purified polynucleotide substrate with the small molecule under conditions suitable for the binary complex to form. The binary complex is then optionally purified to remove any excess small molecule or polynucleotide. The prepared complex (i.e., the competitive ligand) is then added to an assay containing a test compound as part of a ternary complex or is added to the binary complex of test compound and polynucleotide before the biological target is added. If the competitive ligand has a stronger affinity for the target it should compete off the target from the test compound's ternary complex or bind most or all of the target when it is added. If the target remains bound to the test compound or binds to the test compound rather than the competitive ligand, then the test compound as part of a binary complex has a stronger affinity for the target. The small molecule as part of the competitive ligand may be varied in order to screen for more or less potent test compounds. In addition, the amount of the competitive ligand may be varied to create more or less stringent selection criteria. The detection of the bound target may be performed using any of the method described herein (e.g., antibody binding, tagged target).

Kits and Compositions

The present invention also provides kits and compositions useful in the practice of the inventive methods. These kits may include many of the reagents needed to practice the inventive methods. For example, kits or compositions useful in identifying the biological target of an agent known to mediate its effect by binding a polynucleotide may include polynucleotides; solid supports such as affinity resins; buffers; cell lines; media; cell lysates; lysis buffer; purified proteins such as potential targets; positive controls such as a saframycin and its cellular target GAPDH, and cis-platin and its cellular target HMG1; negative controls such as trans-platin and HMG1; materials for SDS-PAGE and staining; and instruction manuals. In certain embodiments, the materials are conveniently packaged together for single or multiple uses. In certain embodiments, the user of the kit would supply the chemical compound(s) for which the biological target is being screened. The user may also provide the polynucleotide when the binding site of the chemical compound on the polynucleotide is known, and the user can provide a polynucleotide specifically designed as a substrate for the chemical compound being studied.

The invention also provides kits and compositions useful in screening for other compounds that act like the saframycins and/or target GAPDH. The composition comprising a ternary complex of a polynucleotide such as dsDNA with a saframycin binding site; a saframycin, ecteinascidin, or analogue thereof; and GAPDH protein is also provided and may be useful for comparison purposes in screening other chemical compounds using the inventive method. The ternary complex of polynucleotide, saframycin or analogues thereof, and GAPDH may also be useful in competition studies with other chemical compounds. As discussed previously, the saframycin molecule is attached to the dsDNA through a covalent but reversible linkage with the exo-amino group of guanine, and the resulting binary complex is recognized by GAPDH. In certain embodiments the polynucleotide or saframycin molecule is attached to a solid support such as an affinity resin or polymeric bead through a covalent linkage or through a non-convalent linkage, such as a streptavidin-biotin interaction, antigen-antibody interaction, or polyHis tag and metal ion interaction. The inventive ternary complex is typically substantially pure and isolated from the cellular materials in which it might normally be found in Nature. Preferably the ternary complex is at least 50% pure, at least 75% pure, at least 80% pure, at least 90% pure, at least 95% pure, or at least 99% pure. The kits used in screening for other chemical compounds that target GAPDH may include saframycins, polynucleotides, a collection of chemical compounds to be tested, a solid support such as an affinity resin or multi-well plate, buffers, solutions, cell lines, cell lysates, lysis buffer, purified GAPDH, antibodies directed against GAPDH, a ternary complex of a saframycin, polynucleotide, and GAPDH for comparison or as a control, software, instruction manuals, and negative controls such as cis-platin. In certain embodiments, the polynucleotide in the kit contains G-rich sequences, and preferably, three base pair sequences of 5'-GGG-3', and 5'-GGPy-3', wherein Py is a pyrimidine. In certain embodiments, the kit is conveniently packaged for single or multiple uses. In certain embodiments, the kit includes the reagents necessary for screening hundreds, thousands, or ten thousands of chemical compounds using high-throughput screening techniques. In kits designed for high-throughput screening, the materials may be packaged for use with fluid-handling robotic systems.

These and other aspects of the present invention will be further appreciated upon consideration of the following Examples, which are intended to illustrate certain particular embodiments of the invention but are not intended to limit its scope, as defined by the claims.

EXAMPLES

Materials and Methods

Buffer A: 100 mM HEPES, pH 7.4.

Buffer B: 20 mM Tris.HCl, pH 7.4, 100 mM NaCl.

Buffer C: 40 mM $NaH_2PO_4$, pH 5.8, 5 mM $MgCl_2$, 0.1 mM $Na_2EDTA$.

Buffer D: 20 mM Tris.HCl, pH 7.4, 15 mM 2-mercaptoethanol, 0.3% Triton X-100, 0.015 mM pepstatin A, 0.025 mM leupeptin, and 1 mM PMSF.

Buffer E: 20 mM Tris.HCl, pH 7.4, 15 mM 2-mercaptoethanol, 0.3% Triton X-100.

Buffer F: 4.5 mM Tris acetate, 1 mM borate, 100 mM NaCl.

1× Binding buffer: 25 mM HEPES, pH 7.9, 3 mM $MgCl_2$, 50 mM KCl, 0.1 mM DTT. (DTT is added right before use.)

Construction of Drug-based Affinity Resin. The amino-modified QAD and its hemiaminal derivative, amino-modified HQ was prepared by coupling SafA synthetic intermediate[11] with 6-(4-Fmoc-amino-n-butoxy)-quinaldic acid followed by Fmoc deprotection. The amino-modified QAD/HQ was purified by reverse-phase HPLC and coupled to AffiGel-15. For the coupling to AffiGel-15, a suspension of AffiGel-15 in isopropanol (5 mL) was washed with isopropanol (2×5 mL). The AffiGel-15 was then suspended in 3 mL of methanol and mixed with a solution of the amino-modified QAD/HQ in methanol (0.5 ml, 1.0 mg/mL). The suspension was mixed by head-to-end inversion for 12 hours. The reaction was stopped by the addition of ethanolamine (200 µl) and subsequent mixing at 23° C. for one hour. The supernatant was removed and the resin was washed with methanol (3×5 ml). The amount of drug coupled to the affinity resin was determined by quantifying the drug that remained in the supernatant using reverse-phase HPLC. The drug-based AffiGel-15 affinity resin was stored in methanol at −20° C.

dsDNA-drug Binary Complex on Drug-based Affinity Resin. The solid support displaying 1 nmol of drug, was washed with Buffer B (2×200 µl) and incubated with 2.5 nmol of double-stranded synthetic 21-mer oligonucleotide (sequence 5'-GGAACCGGGCTCGGGCCAAGG-3') in 150 µl Buffer B at 23° C. for 2 hours. The suspension was pelleted and the supernatant was removed via pipette. The solid was then washed with Buffer B (150 µl, 23° C.) and the supernatant was removed. The solid was incubated in Buffer B 150 µl at 4° C. for 2 days. The supernatant was removed and the solid was again washed with Buffer B 150 µl at 23° C. In order to release the bound DNA, the solid was suspended in Buffer B (150 µl) and the resulting suspension was heated at 95° C. for 30 min. The resin was immediately spun down and the supernatant removed. The supernatant solution was analyzed by reverse-phase HPLC. The amount of ds-oligonucleotide detected in the supernatant from the heating step was taken to be the amount of ds-oligonucleotide coupled to drug on the affinity resin in the form of stable dsDNA-drug binary complex.

Figure 3:
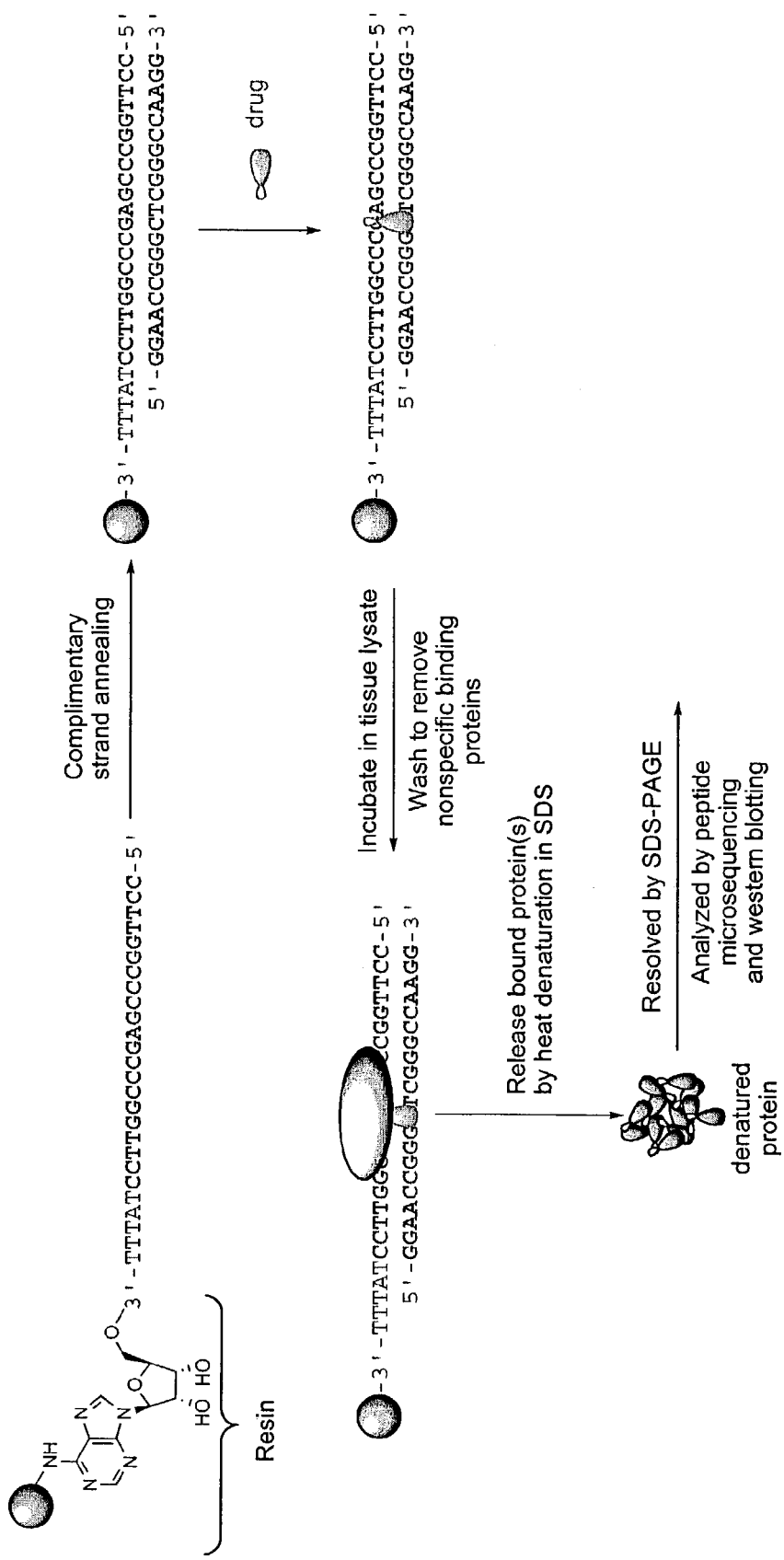
FIG. 3 shows the use of a DNA-drug binary complex as an affinity ligand to identify the protein target of the complex.

Construction of Oligonucleotide-based ToyoPearl-Affinity Resin (FIG. 3). The oligonucleotide 27-mer (5'-TTTTATC-CTTGGCCCGAGC-CCGGTTCC-3') was synthesized on Oligo-Affinity Resin (Glen Research, 24-4001) using standard phosphoramidite chemistry with a modified DNA synthesis protocol on the Expedite 8900 nucleic acid synthesis system. Oligonucleotides were deblocked and deprotected as recommended by the manufacturer. The synthesis of double-stranded oligonucleotide 21-mer on the resin was achieved by annealing the 27-mer with the complementary 21-mer (5'-GGAACCGGGTCTGGGCCAAGG-3'). The concentration of double-stranded 21-mer DNA on the resin was determined by heat denaturing the double strand DNA on a known amount of resin and subsequently determining the concentration of complementary strand in free solution by UV spectrometry.

Characterization of DNA-drug Binary Complex Formation on Affinity Resin by HPLC. The affinity resin displaying 5 nmol of oligonucleotide was washed with Buffer C (2×200 µl) and to the resin was added 95 µl Buffer C. To this reaction mixture was added 5 nmol of drug in a solution of ethanol. The reaction was mixed on an Eppendorf Mixer 5432 at 37° C. for 15 hours. The affinity resin was centrifuged and the supernatant was removed. The affinity resin was then washed with 200 µl ethanol for 5 min to remove the unbound drug. The gel was then incubated in 200 µl Buffer B at 4° C. for 3 hours. The supernatant was aspirated by pipette. To the resin was washed with a solution of ethanol and water (200 µl, 1:1, v/v). In order to release bound drug, the resin was mixed with a solution of ethanol and water (200 µl, 1:1, v/v) and heated at 95° C. for 30 min. The resin was immediately spun down and the supernatant removed. The supernatant solutions obtained from each step of this procedure were analyzed by reverse-phase HPLC to determine the amount of drug in each sample. The amount of drug detected in the supernatant of the last step of the procedure was taken to be the amount of drug coupled to the oligonucleotide on the affinity resin in the form of the DNA-drug binary complex.

Characterization of DNA-drug Binary Complex on Oligonucleotide-based Affinity Resin by DNA-Gel Shift Assay. To a suspension of fluorescent-labeled oligonucleotide modified resin (4 nmol oligonucleotide) in Buffer B (40 µl) was added 20 nmol of HQ or QAD in 2 µl of ethanol; pure ethanol (2 µl) was added to the control experiment. The reaction mixture was incubated at 23° C. for two hours. The resin was then centrifuged and the supernatant was removed. The resin was washed in ethanol (50 µl) for five minutes and washed with Buffer B (50 µl) with gentle mixing for two hours. The resin was then suspended in Buffer B (30 µl) and was exposed to UV light ($\leqq$300 nm) for five minutes. The resin was centrifuged down and the supernatant was mixed with non-denaturing loading buffer (5 µl) and immediately loaded on a 20% non-denaturing polyacrylamide gel at 23° C. The gel was subjected to electrophoresis at 300 V for 2 hours and was visualized by UV light and photographed.

Affinity Chromatography. The drug-oligonucleotide binary complex affinity resin was formed by incubating a suspension of affinity resin displaying 1 nmol of double-stranded oligonucleotide in Buffer B with 10 nmols of drug in DMSO at 37° C. for 15 hours. Bovine brain tissue was homogenized (1:1 w/v) in Buffer D. The homogenate was centrifuged at 100,000 g for 30 min and the supernatant was clarified by filtration through a Bio-Spin® (BioRad) column. The amount of non-specific binding proteins in the homogenate was reduced or "pre-cleared" by incubating 20 mL of the homogenate with 0.4 mL (packed volume) of the toyopearl column funtionalized with ethanolamine at 4° C. for 1 hour. The homogenate was then separated from the ethanolamine-functionalized resin and filtered through a Bio-Spin® (Bio-Rad) column and adjusted to 0.5 M NaCl by addition of 5 M NaCl solution. The filtrate was incubated at 4° C. for 12 hours with the drug-dsDNA affinity resin. After washing the resin three times with Buffer E, the proteins were released from the affinity resin by heat denaturation at 95° C. for 5 min. The proteins were resolved by SDS-PAGE (4–20% gradient gels) and identified by silver staining, peptide microsequencing, and western blotting using mouse anti-rabbit GAPDH as the primary antibody.

Glycolysis Activity. DNA-HQ binary complex in solution was prepared by incubating the 20 nmol (base pair) calf thymus DNA in Buffer B and 10 nmol of HQ in ethanol at 23° C. for 3.5 hours. The mixture was incubated with commercial human erythrocyte GAPDH protein solution in ddH$_2$O (Sigma 6019, 100 µl, 100 µg/ml) for 10 min or 60 min prior to the addition of other components. Glycolysis activity was determined by following the conversion of NAD$^+$ to NADH by monitoring changes in A$_{340}$. (Krebs, E., Rafter, G., and Junge, J.: Yeast Glyceraldehyde-3-Phosphate Dehydrogenase, *J. Biol. Chem.* 200, 479, 1953; incorporated herein by reference)

Southwestern Blot. (Rapley, R. The Nucleic Acid Protocols Handbook, Humana Press, Totowa, N.J.; incorporated herein by reference) Human erythrocyte GAPDH (Sigma 6019) was dissovled in ddH$_2$O (1 mg/ml) and 10 µg of the protein solution was denatured and resolved on 4–20% SDS-PAGE gel at 150 V for one hour. The protein was transferred to a nitrocellulose membrane at 6 V for three hours. The membrane was cut into strips corresponding to each electrophoretic lane and immersed in denaturation buffer (6 M guanidine hydrochloride in 1× Binding buffer) for 10 min at 4° C. The membranes was incubated in 1× Binding buffer at 3 M, 1.5 M, 0.75 M, 0.375 M, and 0.185 M guanidine hydrochloride, each 10 min at 4° C. followed with a wash of 1× Binding buffer for 20 min (each solution 15 ml). The membranes were then incubated in 1× Binding buffer with 3% BSA for one hour at 4° C. and incubated individually with solutions of different dsDNA-drug binary complexes or DNA alone prepared from $^{32}$P-labeled double-stranded oligonucleotide at 4° C. for 24 hours. The membrane was washed with 1× Binding buffer (2×20 ml, each wash 10 min) and dried over filter paper. The membrane was then exposed to X-ray film at −80° C. for 24 hours. The film was fixed and developed.

Cell Fractionation Studies. HeLa S3 cells were grown in DMEM with high glucose (GIBCO) also containing 10% fetal bovine serum (FBS), penicillin G (10 units/ml), and streptomycin (10 µg/ml) at 37° C. with an atmosphere of 5% CO$_2$/95% air. All cellular fractionation experiments were started with HeLa-S3 cells being approximately 40% confluent in a 750 mL culture flask before addition of HQ, which was dissolved in medium and added as a single dose to achieve a final concentration of 15 µM drug in the culture medium. At the end of the specified period of incubation in the drug containing media, the cells were collected by physical scraping and pelletted by centrifugation at 1,000 g for 5 min. Cytoplasmic and nuclear extracts were prepared using the CelLytic™ NuCLEAR™ EXTRACTION KIT (SIGMA). The total protein concentration in each sample was determined by the Bradford Method. Equal amounts of total protein from the cytoplasmic and nuclear enriched fraction lysates were resolved by SDS-PAGE, Western blotted, and probed for GAPDH immunoreactivity.

Confocal Microscopy. Hela-S3 cells were cultured in a 12-well tray in DMEM with high glucose (GIBCO) also containing 10% fetal bovine serum (FBS), penicillin G (10 units/ml), and streptomycin (10 µg/ml) at 37° C. with an atmosphere of 5% CO$_2$/95% air. The cells at 5–10% confluency were washed with 0.5% DMSO in fresh medium (4 ml) or a HQ soluiton of 05% DMSO in fresh medium (12.5 nM, 4 ml) and then incubated with the corresponding medium at 37° C. under 95% air and 5% CO$_2$ for two days (20–40% confluency). The cells on the coverslips were then washed with PBS buffer (2×4 ml, 5 min), fixed by 4% formaldehyde (5 min), permeabalized by 0.1% Triton X-100 (5 min) and 6 M guanidinium chloride (5 min). The coverslip was then exposed to a solution of 0.3% mouse anti-GAPDH antibody (Research Diagnostics Inc), or 2% mouse anti-14-3-3 β antibody (Santa Cruz Biotechnology) in PBS buffer for half an hour. After washing with PBS buffer (3×4 ml, 5 min), the coverslip was exposed to a solution of 0.2% fluorescein goat anti-mouse IgG (Molecular Probe) for half an hour. After washes of the coverslip in PBS buffer (3×4 ml, 5 min), the coverslip was mounted onto a glass slide and visualized by using confocol microscopy.

Removal of NAD$^+$ from GAPDH. Commercial GAPDH (Human erythrocytes: Sigma G6019; Rabbit muscle: Sigma G0763) was dissolved in EDTA buffer (0.005 M, pH 7.8, 4 mg/ml) and centrifuged at 14,000 g. The supernant was collected as GAPDH protein stock solution. GAPDH-bound NAD$^+$ was removed by passing GAPDH protein stock solution through a charcoal-filled pippet chromatography using EDTA buffer (0.005M, pH7.2) as eluent. (Krimsky, I.; Racker, E. Separation of Oxidative from Physphorylative Activity by Proteolysis of Glyceraldehyde-3-phosphate Dehydrogenase, Biochemistry, 2, 512–518, 1963) NAD$^+$ content was determined by measuring A$_{280}$/A$_{260}$ of GAPDH solution. (Seydoux, F.; Bernhard, S.; Pfenninger, O.; Payne, M.; Malhotra, O. P. Preparation and Active-Site Specific Properties of Sturgeon Muscle Glyceraldehyde-3-phosphate Dehydrogenase, Biochemistry, 12, 1973, 4290–4300). GAPDH prepared from charcoal chromatography was diluted to 0.005 mg/ml in 1× bovine brain lysis buffer (0.5 M NaCl) and used as protein solution for affinity chromatography.

GAPDH Protein Down-Regulation Mediated by GAPDH siRNA Transfection. (Ambion 1630) Approximately 24 hours before transfection, non-small cell lung A549 cells were plated in 24-well culture vessel (each well 50,000 cells in 1 ml DMEM media with 10% fetal bovine serum) and cultured at 37° C. under 95% air and 5% $CO_2$. The culture medium was aspirated and the cell monolayer in each well was washed with Opti-MEM I (2×1 ml). To each well was added Opti-MEM I (200 μl) and a solution of control or GAPDH siRNA (50 μl) prepared as described below. The 24-well vessel was tilted four times to mix the solution without shaking. The cells were then cultured at 37° C. under 95% air and 5% $CO_2$ for 6 hours. To each well was added DMEM medium with 10% fetal bovine serum (1 ml) and cultured at 37° C. under 95% air and 5% $CO_2$ for 12, 24, 48, 72, or 96 hours. The cells were washed with Hank's balanced salt solution 2×1 ml and trypsinized by using 200 μl trypsin-EDTA solution/600 μl DMEM medium. The cells were pelleted at 1000 g at 4° C. and washed with sterile PBS buffer 2×1 ml. The cells were suspended in lysis buffer and incubated in ice for 30 min. The solid residue was pelleted at 10,000 g for 10 min and the supernatant was collected as the protein lysate. The protein concentration of the protein lysate was determined by Bradford method (BioRad reagent) and equal amount of total proteins (~10 μg) was resolved by 4–20% SDS-PAGE gel and GAPDH was quantified by western blotting analysis.

GAPDH siRNA Solution for Transfection (15 transfections). In a sterile 1.5-ml Eppendorf tube, dilute 15 μl of siPORT Lipid dropwise into Opti-MEM I medium for a final volume of 120 μl. Vortexed well and incubated at 23° C. for 30 min. In a second sterile 1.5-ml Eppendorf tube, diluted 15 μl of 20 μM GAPDH siRNA into Opti-MEM I medium for a final volume of 630 μl and added this diluted GAPDH siRNA into the above diluted siPORT Lipid, mixed by pippetting. The mixture was incubated at 23° C. for 20 min before addition to cells. Control solution was prepared following the same procedure except that control siRNA, which had the same base composition as GAPDH siRNA but different sequence, was used.

$GI_{50}$ for QAD and Cisplatin in GAPDH siRNA transfected A549 Cells. A549 cells were transfected with GAPDH siRNA or contro siRNA following the procedure described above. Six hours after transfection, the cells were cultured in DMEM medium with QAD/Cisplatin at defined concentration at 37° C. under 95% air and 5% $CO_2$ for 72 hours. The amount of viable cells in each well were determined by measuring $A_{595}$ using MTS and normalized based on the amount of cells in the well w/o drug treatment. (Promega CellTiter96AQNON-Radioactive Cell Proliferation Assay Kit, G5421) Cell survival was plotted as a function of normalized viable cells to drug concentration and $GI_{50}$ was extrapolated.

Results and Discussion

Figure 1B:
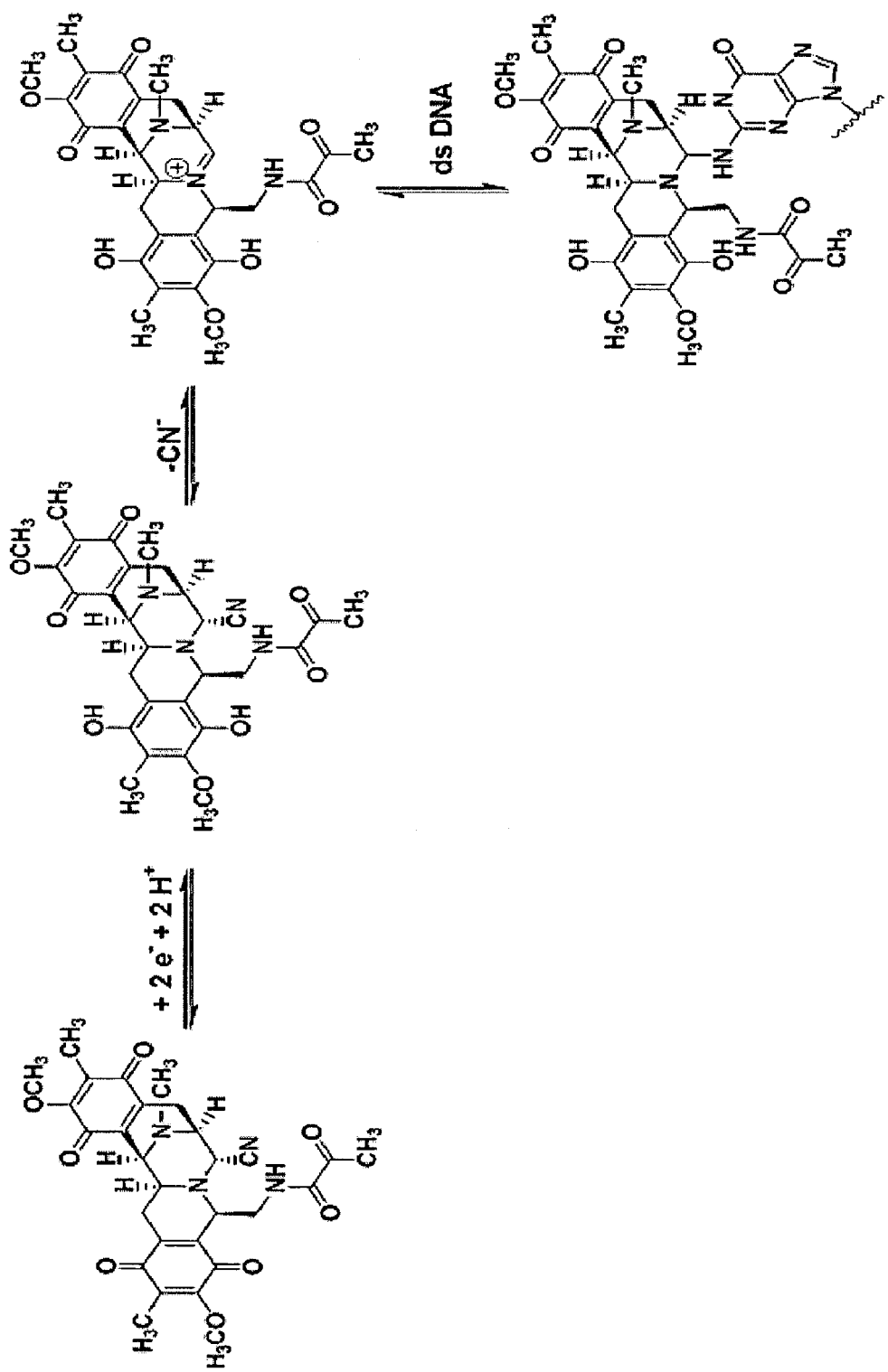
FIG. 1B shows the alkylation of DNA by (−)-saframycin A at a guanine residue. The DNA alkylation process is reversible and the DNA-drug adduct is labile. The alkylation reaction has been found to be sequence selective as the drug prefers to bind to certain three base pair motifs such as 5'-GGG-3', 5'-GCC-3', and 5'-GGPy-3', wherein Py is a pyrimidine.
Figure 2:
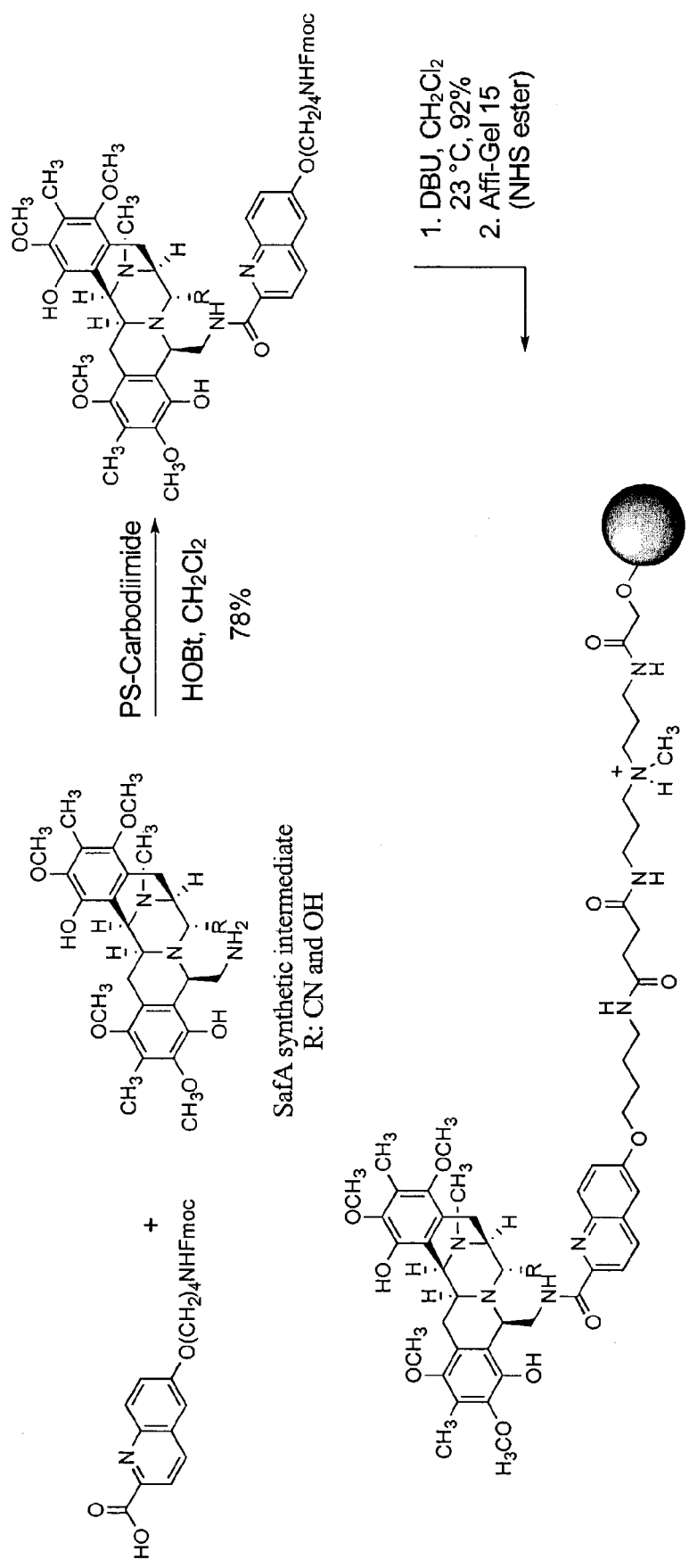
FIG. 2 shows the scheme for constructing a drug-based AffiGel-15 affinity resin.

Affinity Chromatography Using Drug-Based Affinity Resin:

Initially we set out to determine if there was a protein or proteins that interacted directly with our compounds of interest. To this end, two different drug-AffiGel-15 affinity resins were constructed by coupling modified QAD and HQ (FIG. 1) to AffiGel-15. (FIG. 2) The loading level of drug to the affinity resin was determined indirectly by quantifying the amount of drug remaining uncoupled to the resin. The drug-based affinity resin was incubated in bovine brain lysate, washed scrupulously, and heat denatured to release bound proteins. However, no protein was observed to bind selectively to QAD or HQ modified resin. This suggested that QAD/HQ alone is not recognized by any proteins at a detectable level. Since it was well established that an important event in the biological mechanism of the parent compound, Saframycin A, is binding to DNA, we wanted to explore if any protein(s) may recognize the small molecule-DNA complex formed from our compounds of study. Initially, we tried to construct a DNA-drug binary complex on the drug-based affinity resin. When the drug-based affinity resin was incubated with double-stranded oligonucleotide under various reaction conditions, no oligonucleotide was detected to bind to drug-based affinity resin, indicating inefficient formation of DNA-drug binary complex on the drug-based affinity resin. We envision that the attachment of the small molecules to solid resin may interfere the binding and alkylation of QAD/HQ to free dsDNA. Such an issue would be overcome if dsDNA was linked to solid resin and free small molecule was used to form the DNA-drug binary complex. The second advantage of attaching dsDNA to solid resin is that DNA-drug binary complex from DNA-based resin mimics free DNA-drug binary complex better than such complex formed from drug-based resin. The third advantage of using DNA-based resin is that different saframycin A analogues and other DNA alkylating agents could be easily adapted to this system in search of protein targets while such an extension is time-consuming and problematic if drug-based resin strategy is employed. We, therefore, designed an affinity chromatography assay that would employ the drug-DNA complex as an affinity ligand on DNA-based affinity resin. Our affinity chromatography design is outlined in FIG. 3. First, a single stranded oligonucleotide is synthesized off of an affinity support. Second, a complementary strand is annealed to form the double-stranded oligonucleotide affinity resin. Finally, this affinity resin is incubated with small molecules of interest to form the dsDNA-drug affinity resin.

Figure 4:
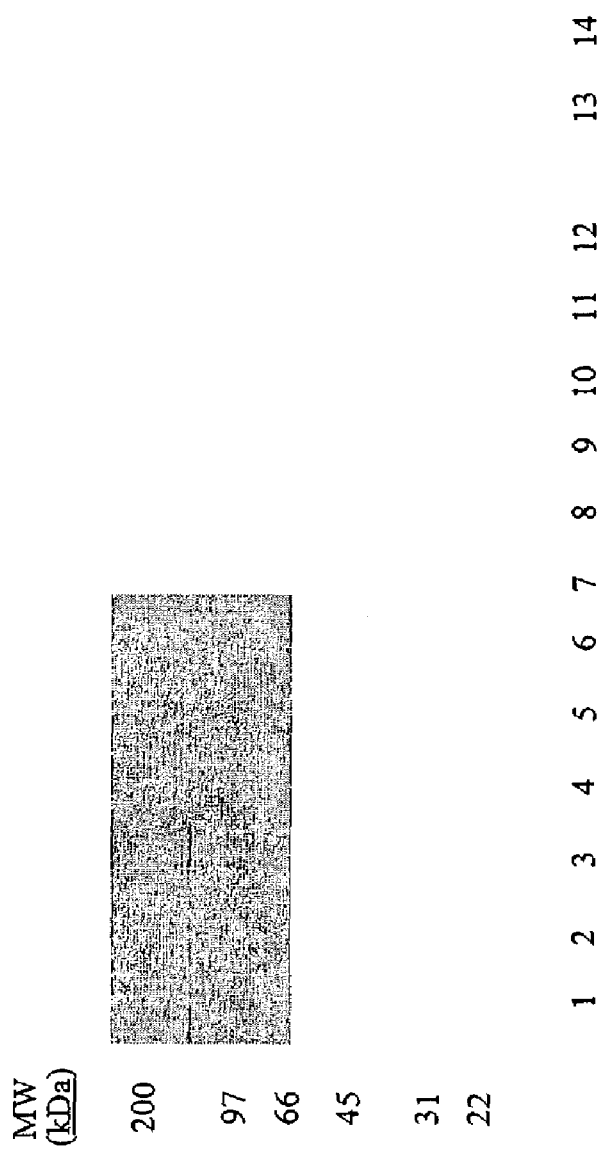
FIG. 4 is a photograph of a silver-stained SDS-PA gel showing the affinity chromatography results. The affinity matrix was incubated in bovine brain lysate at 4° C., washed extensively, and heat denatured to release bound proteins. Lane 1: molecular weight standard; Lane 2: dsDNA resin: control matrix to lane 3, 4, and 5; Lane 3: QAD alkylated dsDNA resin; Lane 4: QAD alkylated dsDNA resin with 40 equivalents of QAD/dsDNA complex free in solution; Lane 5: Pt 650 alkylated dsDNA resin; Lane 6: dsDNA resin: control matrix to lane 7; Lane 7: SafA alkylated dsDNA resin; Lane 8: dsDNA resin control matrix to lane 9; Lane 9: MMC alkylated dsDNA resin; Lane 10: dsDNA resin control matrix to lane 11 and 12; Lane 11: cis-platin alkylated dsDNA resin; Lane 12: trans-platin alkylated dsDNA resin; Lane 13: dsDNA resin control matrix to lane 14; Lane 14: bispyridal alkylated dsDNA.

Cisplatin Results:

At the start, we sought to determine if our DNA-based affinity chromatography system would yield the correct results for an established system where a protein has been identified to interact with a small molecule bound to DNA. Thus, cisplatin was chosen as a test case. In 1992, Lippard et al. determined that HMG1 protein bound to DNA that had been alkylated with cisplatin. Furthermore, they discovered that DNA alkylated with clinically inactive transplatin did not recruit HMG1, supporting the biological relevance of this interaction. In order to test if our assay could identify this interaction, affinity resins, using both cisplatin and transplatin, were prepared and incubated in pre-cleared bovine brain lysate, washed scrupulously, and heat denatured to release bound proteins. A 31-kDa protein was realized to bind specifically to the drug-dsDNA binary complex formed from ds-oligonucleotide resin alkylated with cisplatin (FIG. 4, lane 11). The protein was identified as HMG1 by western blotting analysis and protein mass spectrometry sequencing. Moreover, transplatin did not recruit any protein drug dependently (FIG. 4, lane 12).

QAD, Pth-650, Saf A:

Upon the successful identification of the protein that recognizes the cisplatin/DNA adduct, we were poised to use this system to determine if there was a protein or proteins that interacted with the drug/DNA adducts formed from our compounds of study. Using the affinity chromatography assay, a 37-kDa protein was found to bind specifically to the drug-oligonucletide binary complexes formed from ds-oligonucleotide resin alkylated with QAD, Pt 650, and SafA (FIG. 4, lanes 3, 5, and 7). HQ also recruited the same protein when used in the affinity chromatography assay (results not shown). Furthermore, we demonstrated, for the case of QAD, that the protein could be completely competed off by adding 40 equivalent of free competitive ligands to the binding assay (FIG. 4, lane 4). The 37-kDa binding protein was later identified as GAPDH by protein mass spectrometry sequencing and confirmed by western blotting analysis.

Negative Controls (Cisplatin and Mitomycin C):

Importantly, GAPDH did not bind to drug-dsDNA binary complexes formed from ds-oligonucleotide resin alkylated with cisplatin, transplatin, and mitomycin C (FIG. 4, lane 11, 12, and 9). The fact that GAPDH did not bind to DNA alkylated with cisplatin or mitomycin C indicates that there is a unique aspect of the QAD-dsDNA complex which is recognized by GAPDH and it is not merely because a guanosine residue has been alkylated by a small molecule.

Figure 5A:
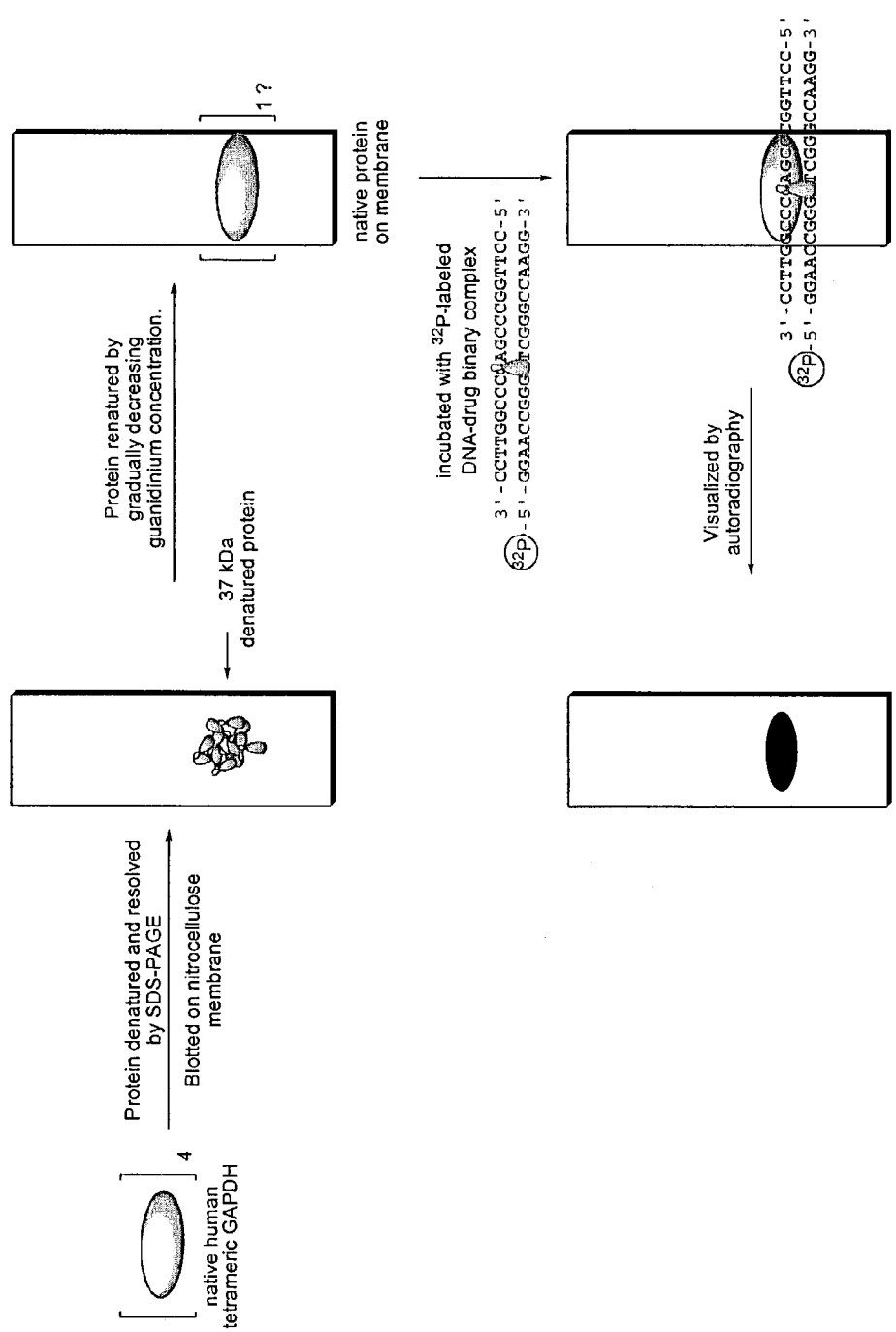
FIG. 5A is a schematic of the Southwestern blot technique.
Figure 5B:
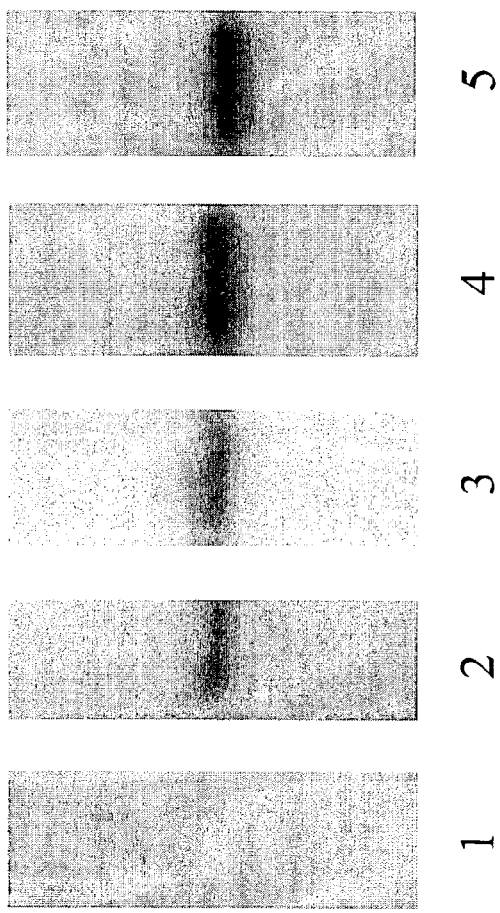
FIG. 5B shows the Southwestern blot results with GAPDH and saframycins. The membranes with GAPDH were incubated with the various $^{32}$P-labeled dsDNA-drug complexes. Lane 1: free dsDNA control; Lane 2: HQ alkylated dsDNA; Lane 3: QAD alkylated dsDNA; Lane 4: Pt 650 alkylated dsDNA; Lane 5: SafA alkylated dsDNA.

Southwestern Blot:

In order to confirm the specific interaction of GAPDH with the dsDNA-drug binary complex formed from saframycin A and its analogues, the southwestern blot technique was employed. FIG. 5 highlights the principle of the southwestern blot. First, human GAPDH was resolved on a denaturing gel and transferred to a nitrocellulose membrane. The protein was renatured on the membrane by washing it in decreasing concentration of gaunidine hydrochloride. Consequently, no radioactivity was detected on the membrane when probed with $^{32}P$ labeled DNA alone indicating DNA itself, under the reaction conditions, did not interact with GAPDH on the membrane. However, when the membrane was probed using $^{32}P$ labeled DNA alkylated with QAD, Pth-650, and SafA, radioactivity was detected on a portion of the membrane corresponding to GAPDH protein band, indicating a specific interaction of dsDNA-drug binary complex with GAPDH on the membrane. These results further confirmed the specific recognition of dsDNA-drug binary complex by GAPDH. Southwestern blot results also established that there is a direct interaction of GAPDH with DNA-drug binary complex. The southwestern blot results in conjunction with the glycolysis results suggested that the GAPDH specifically binding to DNA drug binary complex is not the tetrameric form. Such GAPDH is more likely to be monomeric as GAPDH renatured on the membrane is less likely to oligomerize.

Affinity Chromatography Using Monomeric (Needs Characterization) GAPDH:

In an attempt to characterize the GAPDH isolated from the affinity chromatography, GAPDH was prepared and employed in the affinity chromatography experiments. Monomeric GAPDH was prepared from commercial tetrameric GAPDH by removing $NAD^+$ using charcoal. Based on $A_{280}/A_{260}$, $NAD^+$ in GAPDH was reduced from 0.8 equivalent to 0.075 equivalent per monomeric GAPDH through charcoal treatment. The apo-enzyme was diluted to 0.005 mg/ml in 1× bovine brain lysis buffer (0.5 M NaCl) and was employed as a protein solution for affinity chromatography experiment. This GAPDH was found to bind specifically to the DNA-drug binary complex. The addition of 1 equivalent of $NAD^+$ per monomeric GAPDH into this GAPDH protein solution, however, abolished its binding to DNA-drug binary complex. Furthermore, commercial GAPDH at this concentration was not observed to bind to DNA-drug binary complex.

DNA-Drug Interference with GAPDH Glycolysis Activity

Figure 7:
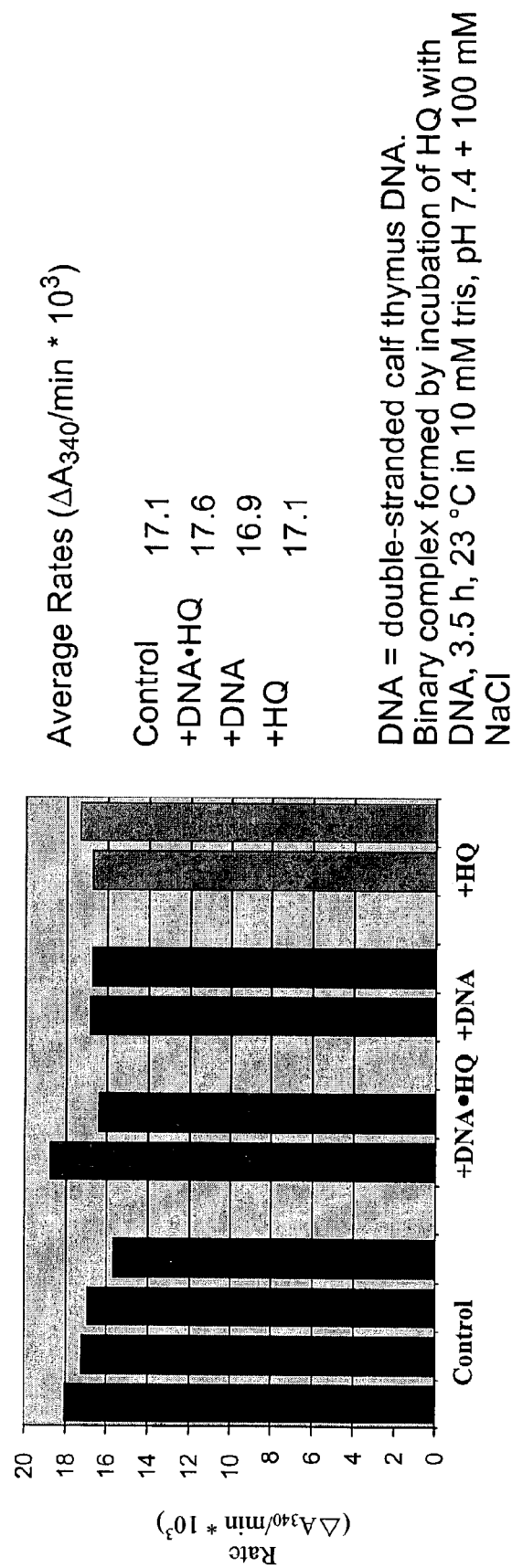
FIG. 7 is a bar graph showing the results of assays for the effect of the DNA-drug binary complex on GAPDH glycolysis activity. The addition of drug, DNA, or dsDNA-drug complex to the glycolysis mixture showed no observable changes to the glycolytic activity of GAPDH.

To further characterize the GAPDH isolated from the affinity chromatography experiment, the potential interference of drug, DNA, or dsDNA-drug complex to the glycolysis activity of GAPDH were examined. Commercial human GAPDH was used as it was and glycolysis activity was determined by measuring the conversion of $NAD^+$ to NADH following the absorbance decrease at 340 nm. The addition of drug, DNA, or dsDNA-drug complex to the glycolysis mixture introduces no observable changes to the glycolytic activity of GAPDH. (FIG. 7) These results suggested that the anticancer mechanism of QAD is not involved with interference in glycolysis and the GAPDH isolated from the affinity chromatography might be different from the commercial tetrameric GAPDH. Possible protein sequence/amino acid modification novel to the GAPDH isolated from affinity chromatography was explored by analyzing such GAPDH using trypsin digestion and mass spectrometry. No protein sequence difference or novel amino acid modification was detected. Such possibility, however, can not be excluded due to the relatively small amount of GAPDH we prepared from affinity chromatography and the sensitivity of the mass spectrometry technique.

Figure 6:
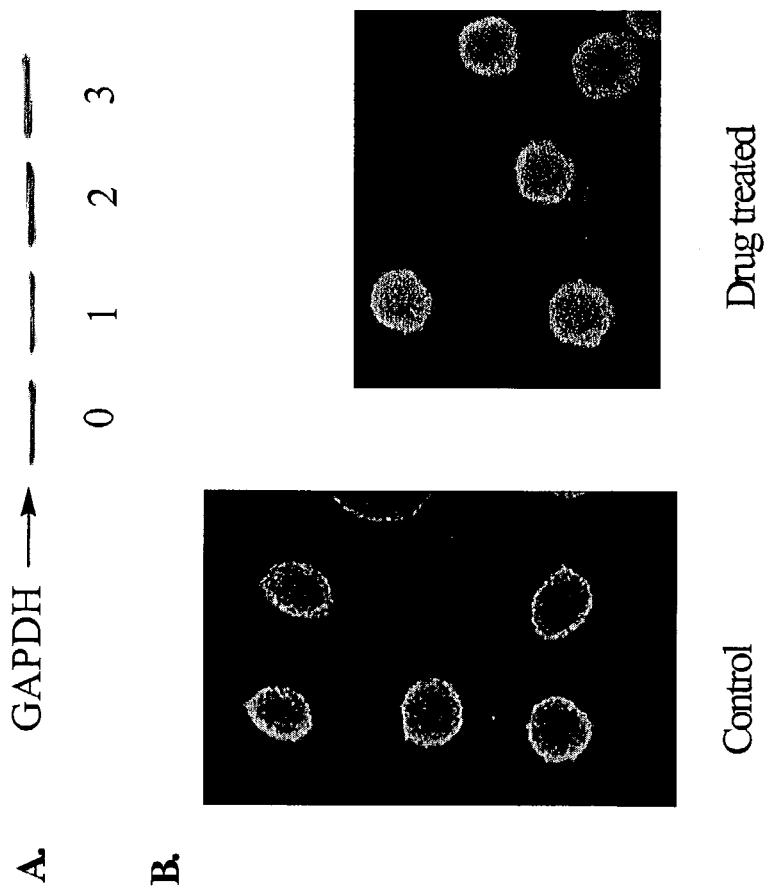
FIG. 6 shows the nuclear GAPDH translocation after HQ treatment in HeLa-S3 cells. A. Accumulation of GAPDH in nuclear extracts from HeLa cells at 1 day, 2 days, and 3 days after treatment with 17.5 nM HQ. B. Confocal laser scanning micrograph of optical sections of HeLa-S3. Control was treated with 0.5% DMSO for 2 days; drug treated cells were incubated with 17.5 nM HQ in 0.5% DMSO for 2 days.

Translocation as a Biochemical Effect Involving GAPDH Produced Upon Drug Treatment in Human HeLa-S3 Cells:

With the in vitro results in hand, we wanted to investigate if there were any observable biochemical effects involving GAPDH in vivo upon drug treatment. We initially investigated if translocation of GAPDH from the cytosol to the nucleus would result from the treatment of HeLa-S3 cells with the anti-tumor agents of interest. To this end, cellular fractionation studies were performed on HeLa-S3 cells treated with HQ for 0, 1, 2, and 3 days. The cytosolic and nuclear fractions of these four cell populations were resolved by SDS-PAGE, transferred to nitrocellulose paper, and assayed for immunoreactivity with GAPDH antibody. FIG. 6 shows an increase in the amount of GAPDH in the nucleus after the second and third day of drug treatment indicating translocation of GAPDH from the cytosol to the nucleus of the cell.

Furthermore, confocal microscopy studies were undertaken to visualize the GAPDH translocation process. In our studies, two populations of cells were cultured for an equal amount of time on confocal microscope coverslips. The control population was treated with growth media containing 0.5% DMSO for two days before fixation, and the other population was treated with growth media containing HQ dissolved in DMSO to a final concentration of 20 nM. FIG. 6 is a summary of the results obtained from the microscopy experiments. The images denote that the drug treated cell population contains more GAPDH in the nucleus than the control cell population.

The translocation studies will be used in conjunction with relevant literature citations to provide circumstantial evidence for the biological relevance of the GAPDH-drug/DNA interaction. The two most important literature citations that support our argument are: (1) the paper that demonstrates that GAPDH plays a role in apoptosis, and (2) the paper that identifies GAPDH as a component in a complex that recognizes thiopurines incorporated into DNA. In both of these papers, GAPDH is shown to translocate from the cytosol into the nucleus. Thus, our observation of translocation of GAPDH upon drug treatment suggests that perhaps GAPDH is playing a similar role in our system.

GAPDH siRNA Silencing Renders A549 Tumor Cells Resistant to QAD not Cisplatin

Figure 8:
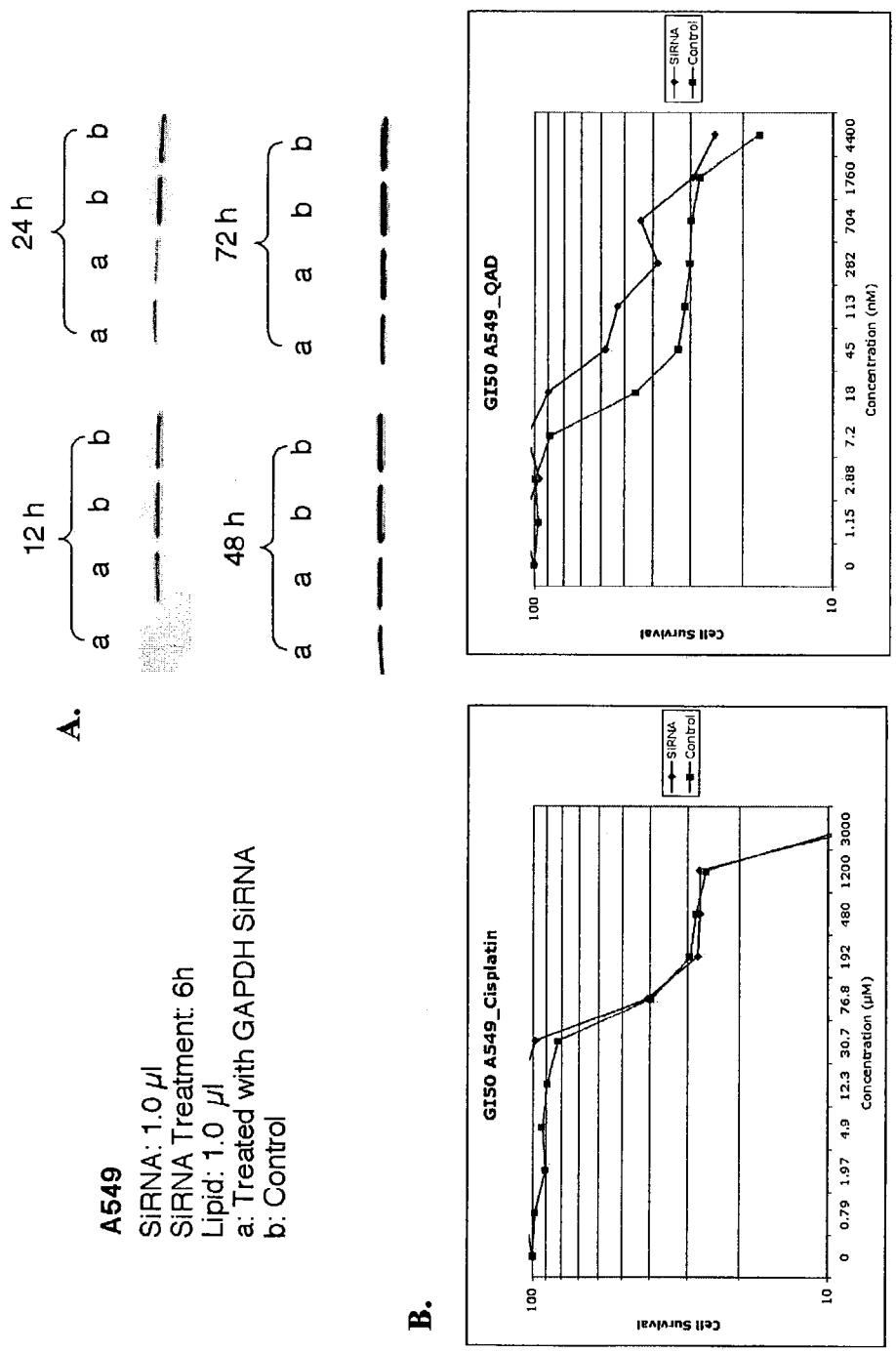
FIG. 8 shows GAPDH siRNA silencing experiments. GAPDH siRNA silencing renders A549 tumor cells resistant to QAD not cis-platin.

We sought to determine if there was a direct connection between the biological mechanism of the small molecules and the regonition of their DNA complexes by GAPDH. Therefore we thought to use siRNA directed against GAPDH to down-regulate the expression level of GAPDH in A549 cells and then subsequently observe if there was a change in the sensitivity of the cells to the drugs. By transfecting GAPDH siRNA into A549 cells in one dosage, we were able to transiently reduce GAPDH expression level to around 50% over the time span of 24 hours to 72 hours after transfection. As indicated by FIG. 8, GAPDH siRNA transfected cells, when treated with cisplatin, have nearly the same sensitivity to the drug as the cells transfected with control siRNA suggesting that GAPDH siRNA treatment and GAPDH protein down-regulation did not change cells' viability to cisplatin. In a parallel set of experiments, however, GAPDH siRNA transfected cells were more resistant ($GI_{50}$ increased by 7–9 fold) to QAD than the cells transfected with control siRNA. The increase of $GI_{50}$ for QAD in GAPDH-reduced cells in conjunction with cis-platin $GI_{50}$ results suggested that GAPDH reduction is specifically responsible for the cell resistance to QAD, indicating that GAPDH is involved in mode of QAD's anticancer action in vivo.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

---

The invention claimed is:

1. A method of identifying a cellular target, the method comprising steps of:
   providing a solid support;
   providing a polynucleotide;
   providing a chemical compound, wherein the chemical compound is not a polynucleotide;
   attaching the polynucleotide to the solid support;
   contacting the chemical compound with the polynucleotide attached to the solid support under suitable conditions to form a binary complex between the chemical compound and the polynucleotide;
   contacting the binary complex attached to the solid support with a cell lysate under suitable conditions for a biological target of the binary complex to bind; and
   identifying biological target bound to binary complex.

2. The method of claim 1, wherein the solid support is a resin.

3. The method of claim 1, wherein the solid support is a plastic or glass plate.

4. The method of claim 1, wherein the polynucleotide is DNA.

5. The method of claim 1, wherein the polynucleotide is a modified DNA.

6. The method of claim 1, wherein the polynucleotide is RNA.

7. The method of claim 1, wherein the polynucleotide is a modified RNA.

8. The method of claim 1, wherein the polynucleotide contains a sequence of bases recognized by the chemical compound.

9. The method of claim 1, wherein the polynucleotide comprises up to 100 bases.

10. The method of claim 1, wherein the polynucleotide comprises up to 50 bases.

11. The method of claim 1, wherein the polynucleotide comprises up to 30 bases.

12. The method of claim 1, wherein the polynucleotide is double-stranded.

13. The method of claim 1, wherein the polynucleotide is single-stranded.

14. The method of claim 1, wherein the chemical compound is a natural product.

15. The method of claim 1, wherein the chemical compound is a small molecule.

16. A method of identifying a cellular target, the method comprising steps of:
   providing a solid support;
   providing a polynucleotide;
   providing a chemical compound, wherein the chemical compound is a saframycin, a saframycin analogue, or ecteinascidin 743;
   attaching the polynucleotide to the solid support;
   contacting the chemical compound with the polynucleotide attached to the solid support under suitable conditions to form a binary complex between the chemical compound and the polynucleotide;
   contacting the binary complex attached to the solid support with a cell lysate under suitable conditions for a biological target of the binary complex to bind; and
   identifying biological target bound to binary complex.

17. The method of claim 16, wherein the chemical compound is saframycin A.

18. The method of claim 16, wherein the chemical compound is ecteinascidin 743.

19. A method of identifying a cellular target, the method comprising steps of:
   providing a solid support;
   providing a polynucleotide;
   providing a chemical compound, wherein the chemical compound is a protein or peptide;
   attaching the polynucleotide to the solid support;
   contacting the chemical compound with the polynucleotide attached to the solid support under suitable conditions to form a binary complex between the chemical compound and the polynucleotide;
   contacting the binary complex attached to the solid support with a cell lysate under suitable conditions for a biological target of the binary complex to bind; and
   identifying biological target bound to binary complex.

20. A method of identifying a cellular target, the method comprising steps of:
   providing a solid support;
   providing a polynucleotide;
   providing a chemical compound, wherein the chemical compound alkylates the polynucleotide;
   attaching the polynucleotide to the solid support;
   contacting the chemical compound with the polynucleotide attached to the solid support under suitable conditions to form a binary complex between the chemical compound and the polynucleotide;
   contacting the binary complex attached to the solid support with a cell lysate under suitable conditions for a biological target of the binary complex to bind; and
   identifying biological target bound to binary complex.

21. The method of claim 1, wherein the chemical compound covalently binds to the polynucleotide.

22. The method of claim 1, wherein the suitable conditions are physiological conditions.

23. The method of claim 1, wherein the suitable conditions includes a pH between 7.2 and 7.5.

24. The method of claim 1, wherein the suitable conditions include a temperature ranging from 20–40° C.

25. The method of claim 1, wherein the suitable conditions include a temperature of approximately 37° C.

26. The method of claim 1, wherein the suitable conditions include a temperature of approximately 25° C.

27. The method of claim 1, wherein the cell lysate is a human cell lysate.

28. The method of claim 1, wherein the cell lysate is a human tumor cell lysate.

29. The method of claim 1, wherein the cell lysate is derived from a tissue or organ.

30. The method of claim 1, wherein the cell lysate is a mammalian cell lysate.

31. The method of claim 1, wherein the cell lysate is a yeast cell lysate.

32. The method of claim 1, wherein the cell lysate is a bacterial cell lysate.

33. The method of claim 1, wherein the step of identifying comprises sequencing the target.

34. A method of identifying a cellular target, the method comprising steps of:
providing a solid support;
providing a polynucleotide;
providing a chemical compound, wherein the chemical compound is not a polynucleotide;
attaching the chemical compound to the solid support;
contacting the polynucleotide with the chemical compound attached to the solid support under suitable conditions to form a binary complex between the chemical compound and the polynucleotide;
contacting the binary complex attached to the solid support with a cell lysate under suitable conditions for a biological target of the binary complex to bind; and
identifying biological target bound to the binary complex.

35. A method of identifying a cellular target, the method comprising steps of:
providing a solid support;
providing a polynucleotide;
providing a chemical compound of structure (I):

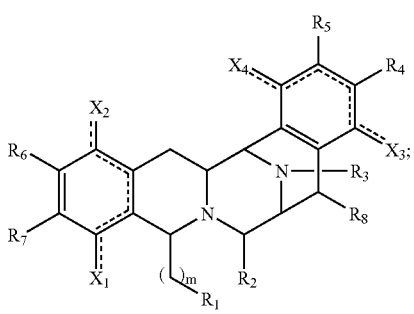

(I)

wherein $R_1$ is $NR_AR_B$, $—OR_A$, $—SR_A$, $—C(=O)R_A$, $—C(=S)R_A$, $—S(O)_2R_A$, or an aliphatic, heteroaliphatic, aryl, heteroaryl, (aliphatic)aryl, (aliphatic)heteroaryl, (heteroaliphatic)aryl, or (heteroaliphatic)heteroaryl moiety, wherein each occurrence of $R_A$ and $R_B$ is independently hydrogen, $—(C=O)R_C$, $—NHR_C$, $—(SO_2)R_C$, $—OR_C$, or an aliphatic, heteroaliphatic, aryl, or heteroaryl moiety, or $R_A$ and $R_B$, when taken together form an aryl, heteroaryl, cycloaliphatic, or cycloheteroaliphatic moiety, wherein each occurrence of $R_C$ is independently hydrogen, $—OR_D$, $—SR_D$, $—NHR_D$, $—(C=O)R_D$, or an aliphatic, heteroaliphatic, aryl, or heteroaryl moiety, wherein each occurrence of $R_D$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;
wherein $R_2$ is hydrogen, $—OR_E$, $=O$, $—C(=O)R_E$, $—CO_2R_E$, $—CN$, $—SCN$, halogen, $—SR_E$, $—SOR_E$, $—SO_2R_E$, $—NO_2$, $—N(R_E)_2$, $—NHC(O)R_E$, or an aliphatic, heteroaliphatic, aryl, or heteroaryl moiety, wherein each occurrence of $R_E$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;
wherein $R_3$ is hydrogen, a nitrogen protecting group, $—COOR_F$, $—COR_F$, $—CN$, or an aliphatic, heteroaliphatic, aryl, or heteroaryl moiety, wherein each occurrence of $R_F$ is independently hydrogen, a protecting group, or an aliphatic, heteroaliphatic, aryl, heteroaryl, alkoxy, aryloxy, alkylthio, arylthio, heteroaryloxy, or heteroarylthio moiety;
wherein $R_4$ and $R_6$ are each independently hydrogen, or an aliphatic, heteroaliphatic, aryl, heteroaryl, acyl, alkoxy, aryloxy, alkylthio, arylthio, heteroaryloxy, or heteroarylthio moiety;
wherein $R_5$ and $R_7$ are each independently hydrogen, $—OR_G$, $—C(=O)R_G$, $—CO_2R_G$, $—CN$, $—SCN$, halogen, $—SR_G$, $—SOR_G$, $—SO_2R_G$, $—NO_2$, $—N(R_G)_2$, $—NHC(O)R_G$, or an aliphatic, heteroaliphatic, aryl or heteroaryl moiety, wherein each occurrence of $R_G$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;
wherein $R_8$ is hydrogen, alkyl, $—OH$, protected hydroxyl, $=O$, $—CN$, $—SCN$, halogen, $—SH$, protected thio, alkoxy, thioalkyl, amino, protected amino, or alkylamino;
wherein m is 0–5;
wherein $X_1$, $X_2$, $X_3$ and $X_4$ are each independently hydrogen, $—OR_H$, $=O$, $—C(=O)R_H$, $—CO_2R_H$, $—CN$, $—SCN$, halogen, $—SR_H$, $—SOR_H$, $—SO_2R_H$, $—NO_2$, $—N(R_H)_2$, $—NHC(O)R_H$, or an aliphatic, heteroaliphatic, aryl, or heteroaryl moiety, wherein each occurrence of $R_H$ is independently hydrogen, a protecting group, or an aliphatic, heteroaliphatic, aryl, heteroaryl, acyl, alkoxy, aryloxy, alkylthio, arylthio, heteroaryloxy, or heteroarylthio moiety;
whereby if at least either $X_1$ and $X_2$ or $X_3$ and $X_4$ are doubly bonded to the 6-membered ring, then the dotted bonds in either or both of the 6-membered rings represent two single bonds and one double bond, and a quinone moiety is generated, or if at least either $X_1$ and $X_2$ or $X_3$ and $X_4$ are singly bonded to the 6-membered ring, then the dotted bonds in either or both of the 6-membered rings represent two double bonds and one single bond, and a hydroquinone moiety is generated;
whereby each of the foregoing aliphatic, heteroaliphatic and alkyl moieties may independently be substituted or unsubstituted, branched or unbranched, or cyclic or acyclic, and each of the foregoing aryl or heteroaryl moieties may independently be substituted or unsubstituted;
attaching the polynucleotide to the solid support;
contacting the chemical compound with the polynucleotide attached to the solid support under suitable conditions to form a binary complex between the chemical compound and the polynucleotide;
contacting the binary complex attached to the solid support with a cell lysate under suitable conditions for a biological target of the binary complex to bind; and
identifying biological target bound to binary complex.

* * * * *

SEQUENCE LISTING

<160> NUMBER OF SEQ ID NOS: 6

<210> SEQ ID NO 1
<211> LENGTH: 335
<212> TYPE: PRT
<213> ORGANISM: Amino acid sequence of GAPDH from human liver

<400> SEQUENCE: 1

Met Gly Lys Val Lys Val Gly Val Asn Gly Phe Gly Arg Ile Gly Arg
 1               5                  10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gly Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val

```
                    225                 230                 235                 240
Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:Double-
      stranded synthetic 21-mer oligonucleotide of dsDNA-drug binary
      complex.

<400> SEQUENCE: 2
ggaaccgggc tcgggccaag g                                              21

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide 27-mer on Oligo-Affinity resin.

<400> SEQUENCE: 3
ttttatcctt ggcccgagcc cggttcc                                        27

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide 21-mer foranneling with 27-mer on resin .

<400> SEQUENCE: 4
ggaaccgggt ctgggccaag g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide 21-mer for Southwestern blot technique.

<400> SEQUENCE: 5
ccttggcccg agcccggttc c                                              21

<210> SEQ ID NO 6
<211> LENGTH: 21
<212> TYPE: DNA
<213> ORGANISM: Artificial Sequence
<220> FEATURE:
```

-continued

```
<223> OTHER INFORMATION: Description of Artificial Sequence:
      Oligonucleotide 21-mer for Southwestern blot technique.

<400> SEQUENCE: 6
ggaaccgggc tcgggccaag g                                              21
```